US008357083B2

(12) United States Patent
Nagai et al.

(10) Patent No.: US 8,357,083 B2
(45) Date of Patent: Jan. 22, 2013

(54) STERILIZATION CONFIRMATION TESTER AND TEST PACK

(75) Inventors: Yuki Nagai, Hachioji (JP); Maiko Shiga, Yokosuka (JP); Yosuke Kanamori, Hachioji (JP); Sawako Sato, Hachioji (JP); Kaori Obi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/093,429

(22) Filed: Apr. 25, 2011

(65) Prior Publication Data
US 2011/0223079 A1  Sep. 15, 2011

Related U.S. Application Data

(60) Division of application No. 11/446,812, filed on Jun. 5, 2006, now abandoned, which is a continuation of application No. PCT/JP2004/018028, filed on Dec. 3, 2004.

(30) Foreign Application Priority Data

Dec. 5, 2003  (JP) ................................ 2003-408333
Dec. 16, 2003  (JP) ................................ 2003-418723

(51) Int. Cl.
*A61B 1/04* (2006.01)

(52) U.S. Cl. ....... 600/133; 435/287.4; 435/31; 422/414; 436/1; 436/2

(58) Field of Classification Search .................. 600/133; 435/31, 287.4; 422/28, 414
See application file for complete search history.

(56) References Cited

U.S. PATENT DOCUMENTS

| 4,914,034 A | * | 4/1990 | Welsh et al. ............... 435/287.4 |
| 5,167,923 A | | 12/1992 | Van Iperen |
| 5,552,320 A | | 9/1996 | Smith |
| 5,750,184 A | | 5/1998 | Imburgia |
| 5,866,356 A | | 2/1999 | Albert et al. |
| 5,872,004 A | | 2/1999 | Bolsen |
| 5,895,627 A | | 4/1999 | Khachatoorian |
| 6,156,267 A | * | 12/2000 | Pai et al. ............................ 422/3 |
| 6,218,189 B1 | | 4/2001 | Antonoplos et al. |
| 6,495,100 B1 | | 12/2002 | Lin et al. |
| 6,773,898 B1 | * | 8/2004 | Nyberg et al. .................. 435/31 |

(Continued)

FOREIGN PATENT DOCUMENTS

EP  0 432 871 A2  6/1991

(Continued)

OTHER PUBLICATIONS

Supplementary European Search Report for Application No. EP 04 81 9926 dated Jan. 4, 2011.

(Continued)

*Primary Examiner* — Matthew J Kasztejna
(74) *Attorney, Agent, or Firm* — Scully, Scott, Murphy & Presser, P.C.

(57) ABSTRACT

The present invention provides a sterilization confirmation tester and a test pack which enables effective sterilization to be confirmed in a simple and sure manner by providing a simulation of the structure of an endoscope and so forth. The sterilization confirmation tester according to the present invention has a function of confirming effective sterilization treatment after sterilization performed by a sterilization apparatus. The sterilization confirmation tester includes a structure corresponding to at least one of the components which form the endoscope.

5 Claims, 15 Drawing Sheets

U.S. PATENT DOCUMENTS

| | | |
|---|---|---|
| 7,090,808 B2 | 8/2006 | Caputo et al. |
| 7,091,042 B2 | 8/2006 | Lemus et al. |
| 7,985,383 B2 * | 7/2011 | Watanabe et al. ............. 422/401 |
| 2001/0000227 A1 * | 4/2001 | Kowanko ........................ 422/33 |
| 2003/0087441 A1 | 5/2003 | Lemus et al. |
| 2003/0215923 A1 | 11/2003 | Witcher et al. |
| 2009/0081767 A1 * | 3/2009 | Ogawa et al. ............. 435/287.4 |

FOREIGN PATENT DOCUMENTS

| | | |
|---|---|---|
| EP | 0 628 814 A1 | 12/1994 |
| EP | 1 052 507 A2 | 11/2000 |
| EP | 1 308 175 A1 | 5/2003 |
| JP | 57-20246 | 2/1982 |
| JP | 3-159650 | 7/1991 |
| JP | 10-201466 | 8/1998 |
| JP | 11-196893 | 7/1999 |
| JP | 2002-355297 | 12/2002 |
| JP | 2003-180804 | 7/2003 |
| WO | WO 03/028772 A1 | 4/2003 |
| WO | WO 2004/084956 A1 | 10/2004 |

OTHER PUBLICATIONS

Japanese Official Action from JP 2003-418723 dated Sep. 9, 2008.
International Search Report dated Mar. 15, 2005 from PCT/JP2004/018028.
U.S. Official Action dated Feb. 4, 2010 from U.S. Appl. No. 11/446,812.
U.S. Official Action dated Jan. 24, 2011 from U.S. Appl. No. 11/446,812.

* cited by examiner

STERILIZATION CONFIRMATION TESTER AND TEST PACK

CROSS REFERENCE TO RELATED APPLICATION

This application is a divisional application of U.S. Ser. No. 11/446,812 filed on Jun. 5, 2006, which is a continuation application of PCT/JP2004/018028 filed on Dec. 3, 2004 and claims the benefit of Japanese Applications No. 2003-408333 filed in Japan on Dec. 5, 2003 and No. 2003-418723 filed in Japan on Dec. 16, 2003, the entire contents of each of which are incorporated herein by their reference.

BACKGROUND OF THE INVENTION

1. Field of the Invention

The present invention relates to a sterilization confirmation tester and test pack, and particularly to a sterilization confirmation tester and test pack including an indicator to confirm sterilization employed in sterilization treatment for medical devices, particularly for a medical device and so forth having a lengthy tubular structure.

2. Description of the Related Art

Conventionally, medical devices used for the purpose of examination or treatment have been subjected to cleansing and sterilization in order to prevent infection and so forth. In particular, in a case of using a medical endoscope, it is indispensable to sterilize the endoscope in a sure manner after the use thereof.

Examples of recently employed sterilization techniques include high-pressure and high-temperature steam sterilization (which will be referred to as "autoclave sterilization" hereafter), and ethylene oxide gas sterilization (which will be referred to as "EOG sterilization" hereafter), which provide the advantage of enabling medical devices to be used immediately after sterilization without involving troublesome operations, and which are also advantageous in terms of running costs.

In sterilization such as autoclave sterilization, EOG sterilization, or the like, in general, operation is performed to confirm whether or not the sterilization treatment has effected satisfactory sterilization.

Examples of conventional confirmation methods for confirming effective sterilization in sterilization treatment using autoclave sterilization or EOG sterilization include: a method in which a tape-shaped chemical indicator (which will also be referred to as "CI" hereafter) is attached to a medical device (sterilization apparatus); and a method in which a sheet-shaped chemical indicator or biological indicator (which will also be referred to as "BI" hereafter) is introduced among the objects to be sterilized.

Examples of the types of the aforementioned BIs and CIs used in conventional sterilization confirmation methods include: a type formed in a tape shape for installation outside of a medical device; and a sheet-shaped type which can be installed at a portion within a medical device (at a portion having a certain space relatively near the opening). Also, examples of the aforementioned CIs include linear type CIs used for lengthy tubular medical devices. Also, testers (test packs) are conventionally known having a configuration in which such a liner type CI is provided within a predetermined tube beforehand, thereby offering a function of confirming effective sterilization.

As a conventional example of such a type of tester, Japanese Unexamined Patent Application Publication No. 2002-355297 has proposed a sterilization confirmation indicator having a configuration in which a flocculent member which has adsorbed a sterilization confirmation indicator component is inserted into a slender tube, thereby providing a function of confirming effective sterilization of the tube.

Also, various proposals have been conventionally presented with respect to the structure of a sterilization confirmation tester in which a biological indicator and a culture medium are integrally formed, which are disclosed in Japanese Unexamined Patent Application Publication No. 10-201466, and so forth, for example.

SUMMARY OF THE INVENTION

The present invention relates to a sterilization confirmation tester for confirming effective sterilization performed by a sterilization apparatus. The sterilization confirmation tester has a structure which corresponds to at least one component of an endoscope.

Also, the test pack according to the present invention includes multiple sterilization confirmation testers each of which has a structure corresponding to at least one of the components which form an endoscope. The aforementioned sterilization confirmation testers are configured so as to have structures each of which corresponds to at least one of the components of the endoscope, and which differ from one another.

DETAILED DESCRIPTION OF THE PREFERRED EMBODIMENT(S)

Description will be made below regarding embodiments according to the present invention with reference to the drawings.

First Embodiment

Figure 1:
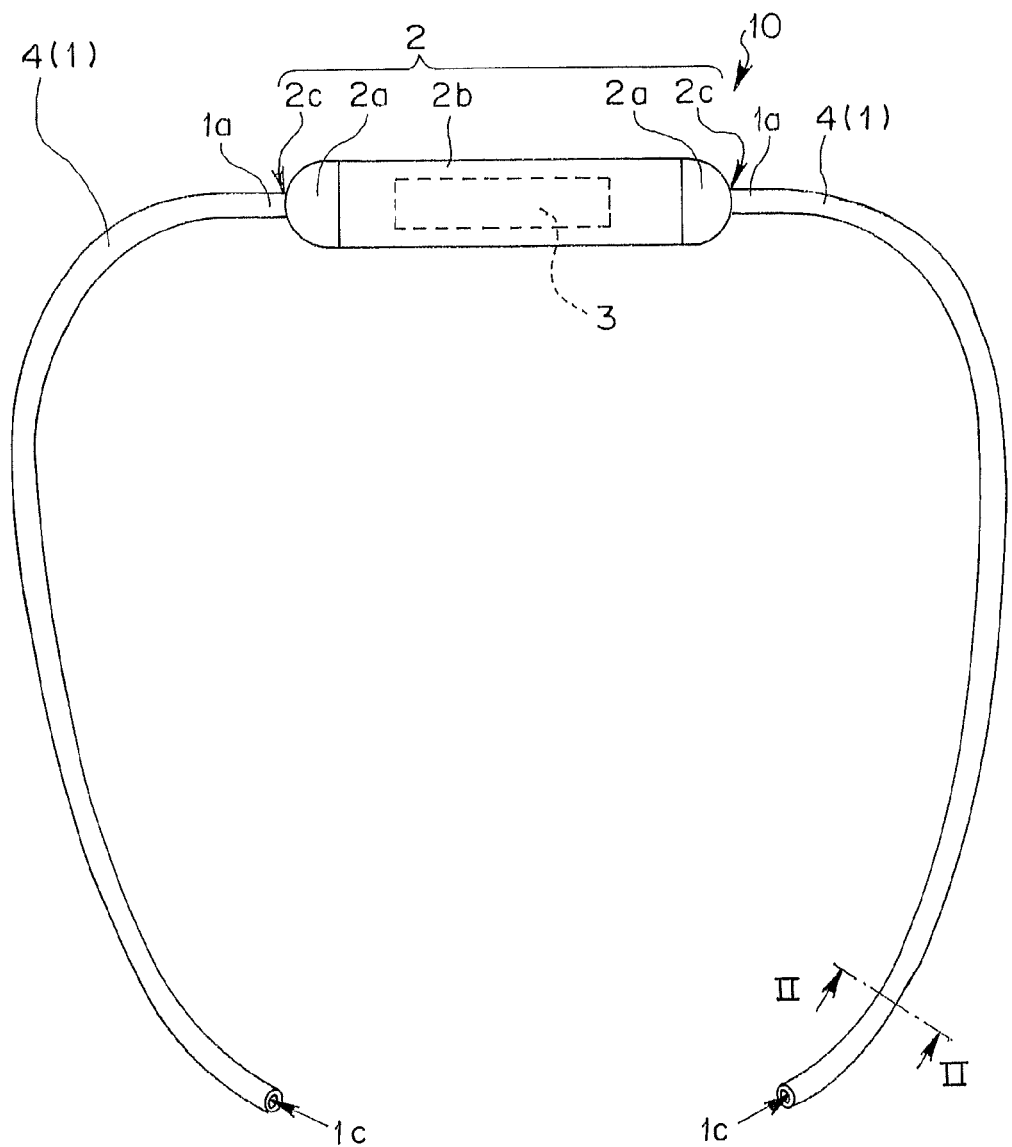
FIG. 1 is an overall diagram which shows a schematic configuration of a sterilization confirmation tester according to a first embodiment of the present invention.
Figure 2:
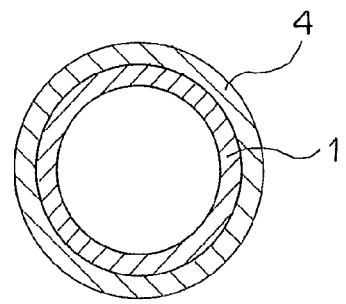
FIG. 2 is an enlarged longitudinal cross-sectional view along line II-II in FIG. 1, which shows the cross-section of a conduit tube and an outer cover member thereof included in the sterilization confirmation tester shown in FIG. 1.

FIG. 1 is an overall diagram which shows a schematic configuration of a sterilization confirmation tester (corresponding to a conduit) according to a first embodiment of the present invention. FIG. 2 is an enlarged longitudinal cross-sectional view along line II-II in FIG. 1, which shows the cross-section of a conduit tube and an outer cover member thereof included in the sterilization confirmation tester shown in FIG. 1.

A sterilization confirmation tester 10 according to the present embodiment is for confirming effective sterilization of a sterilization apparatus. The sterilization confirmation tester 10 has a structure which corresponds to at least one of the components of an endoscope, i.e., which corresponds to a conduit of the endoscope.

Specifically, as shown in FIG. 1, the sterilization confirmation tester 10 comprises: two conduit tubes 1 formed in a slender and tubular shape; an outer cover member 4, which is a coating member, provided so as to cover the outer face of the conduit tubes 1; and an indicator casing 2 configured so as to allow a biological indicator, a chemical indicator 3, or the like (which will simply be referred to as "indicator" hereafter), for example, to be inserted and extracted as desired. Note that the outer cover member 4 does not necessarily have to be provided on the outer face of the conduit tube 1. Furthermore, proximal ends 1a of the two conduit tubes 1 are each provided to both ends of the indicator casing 2. Note that, with such an arrangement, the two conduit tubes 1 are preferably formed in approximately the same shape and size. With such an arrangement, the indicator casing 2 is preferably disposed near the center after the two conduit tubes 1 and the indicator casing 2 are assembled together to form the sterilization confirmation tester 10.

The indicator casing 2 comprises: an indicator storage cylinder 2b which is formed of a transparent or opaque resin or the like and which has openings at both ends thereof; and two caps 2a which enable both ends of the indicator casing 2 to be switched between the opened state and the closed state.

The tip of each of the two caps 2a is configured so as to have an opening 2c which allows the one end 1a of each of the two conduit tubes 1 to be continuously provided. With such an arrangement, the proximal ends 1a of the two conduit tubes 1 are each detachably connected to the tip ends of the two caps 2a. Furthermore, a watertight member (not shown) such as an O-ring or the like is provided to each connection portion where the one end 1a of the conduit tube 1 is connected to the cap 2a. This provides a watertight structure to each of these connection portions.

Furthermore, the caps 2a are detachably provided via the base ends thereof to both ends of the indicator storage cylinder 2b through a watertight member (not shown) such as an O-ring or the like. This also provides a watertight structure to each connection portion between the cap 2a and the indicator storage cylinder 2b.

The conduit tube 1 is formed of a tubular member having a hollow structure in which openings 1c are formed at both ends thereof. The various kinds of the conduit tubes 1 are formed in various kinds of shapes which simulate the shapes (determined by the length, inner diameter, and so forth) of various kinds of endoscope conduits, treatment tools, and so forth. That is to say, in the sterilization confirmation tester 10, the conduit of the conduit tube 1 corresponds to the conduit which is one of the components of a medical device such as an endoscope or the like. Specifically, the conduit tubes 1, each of which is a component corresponding to a conduit, are formed in a shape within a range of the length L from around 300 to 4000 mm, and the inner diameter φ of around 0.1 to 100 mm, for example. With such an arrangement, a desired one of the conduit tubes 1 having a desired shape is selected according to the user's need. On the other hand, the cap 2a (the tip thereof) is configured so as to allow any one of these conduit tubes 1 to be connected thereto in a watertight manner. Thus, the conduits within the two conduit tubes 1 are each connected to the indicator casing 2 so as to communicate with the interior space within the indicator casing 2.

The outer cover member 4 is formed of the same material as that of a flexible hose, operating unit, and so forth of an endoscope, or a material exhibiting the same thermal insulating performance as that of these components, e.g., resin such as urethane, rubber, or the like, for example. The outer cover member 4 according to the present embodiment has a structure in which the outer face of the conduit tube 1 is directly coated with a resin material such as urethane, rubber, or the like, as shown in FIG. 2, thereby providing a coating structure to the outer face of the conduit tube 1.

Description will be made below regarding the operation of the sterilization confirmation tester 10 having such a configuration for confirming effective sterilization.

First, an indicator 3 is installed at a predetermined position in the aforementioned sterilization confirmation tester 10. In this case, the indicator 3 suitable for the sterilization method is selected. Specifically, the caps 2a are detached from the indicator storage cylinder 2b, and the indicator 3 is installed within the indicator storage cylinder 2b. Next, the caps 2a are connected to the indicator 2b. After the connection, each of the caps 2a and the indicator storage cylinder 2b are connected through a watertight member, thereby ensuring that the interior space formed of the caps 2a and the indicator storage cylinder 2b remains watertight.

The sterilization confirmation tester 10 in this state is mounted within a given sterilization apparatus (not shown), and sterilization treatment is executed according to a predetermined procedure. As a result, a sterilization agent such as ethylene oxide gas, steam, or the like, is introduced into the interior of the conduit tube 1 from the opening 1c. Then, the sterilization agent passes through the conduit tube 1, and acts upon the indicator 3 stored in the indicator casing 2.

After this sterilization step, the sterilization confirmation tester 10 is extracted from the sterilization apparatus, and confirmation of effective sterilization is made. This confirmation is made as follows.

First, let us consider a case of employing a biological indicator as the indicator 3. In this case, after the extraction of the indicator 3 from the indicator storage cylinder 2b of the indicator casing 2 in a sterile environment, the indicator 3 is introduced into a predetermined culture medium. After the culturing step, effective sterilization is confirmed based upon whether or not bacteria appear on the culture medium.

Next, let us consider a case of employing a chemical indicator as the indicator 3. In this case, after the extraction of the indicator 3 from the indicator storage cylinder 2b of the indicator casing 2, effective sterilization is confirmed by checking for the change in color of the indicator 3. Note that an arrangement in which the indicator storage cylinder 2b of the indicator casing 2 is formed of transparent resin has the advantage of allowing the change in color of the indicator 3 to be checked without a step for extracting the indicator 3, thereby effecting confirmation of effective sterilization.

The sterilization confirmation tester 10 according to the aforementioned first embodiment has a structure which is a simulation of the tubular structure of an endoscope. This provides confirmation of effective sterilization at a corresponding portion of an endo scope with high reliability.

Description has been made in the above first embodiment regarding an arrangement in which the outer cover member 4, which is provided in the form of a coating to the outer face of the conduit tube 1, is formed of the same material as that of a flexible hose, operating unit, and so forth (conduit in the present embodiment) of an endoscope, or a material exhibiting the same thermal insulating performance as that of these components, e.g., resin such as urethane, rubber, or the like. However, the outer cover member 4 is not restricted to such an arrangement. Also, other arrangements may be made providing the same functions and advantages, as described below, for example, instead of the first embodiment described above.

The sterilization confirmation tester 10 according to the present embodiment can also be applied to other cases in addition to the case described in the present first embodiment. For example, the sterilization confirmation tester 10 can also be applied to confirmation of effective sterilization of a treatment tool (not shown) used together with the endoscope simply by employing the conduit tube 1 formed with the same length, inner diameter, and so forth, as those of the treatment tool. In the same way, embodiments described below can also be applied to confirmation of effective sterilization of any treating tool or the like by employing the structure of the sterilization confirmation tester 10 which is a simulation of the structure of the treatment tool or the like used together with the endoscope.

Second Embodiment

Figure 3:
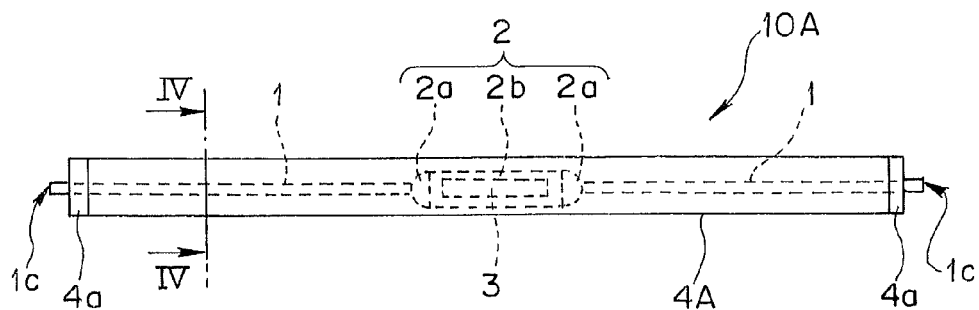
FIG. 3 is an overall diagrams which shows a schematic configuration of a sterilization confirmation tester according to a second embodiment of the present invention.
Figure 4:
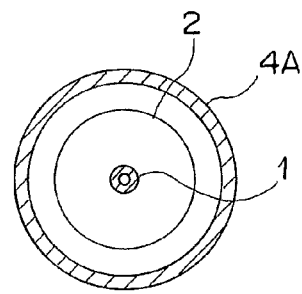
FIG. 4 is an enlarged longitudinal cross-sectional diagram along line IV-IV in FIG. 3, which shows the cross-section of a conduit tube and an outer cover member thereof included in the sterilization confirmation tester shown in FIG. 3.

FIG. 3 and FIG. 4 are diagrams which show a second embodiment of the present invention. Of these, FIG. 3 is an overall diagrams which shows a schematic configuration of a sterilization confirmation tester (for a conduit) according to the present embodiment. FIG. 4 is an enlarged cross-sectional diagram which shows the cross-section of a conduit tube and an outer cover member thereof included in the sterilization confirmation tester shown in FIG. 3, and is a longitudinal cross-sectional view along line IV-IV in FIG. 3.

The second embodiment has generally the same configuration as that of the first embodiment described above, except for the outer cover member. Accordingly, the same components as those of the aforementioned first embodiment are denoted by the same reference numerals, description thereof will be omitted, and description will be made below regarding only the different components.

As shown in FIG. 3, a sterilization confirmation tester 10A according to the present embodiment comprises the two conduit tubes 1, the indicator casing 2, the indicator 3, and an outer cover member 4A. Of these, the conduit tubes 1, the indicator casing 2, and the indicator 3 are the same as those of the aforementioned first embodiment.

The outer cover member 4A according to the present embodiment is configured so as to allow an assembly formed of the indicator casing 2 storing the indicator 3 and the two conduit tubes 1 to be detachably mounted therewithin, in a state in which the indicator casing 2 and the two conduit tubes 1 are continuously provided, as shown in FIG. 3. Accordingly, as shown in FIG. 3, the components corresponding to the conduit of an endoscope, i.e., the two conduit tubes 1 are enclosed within the outer cover member 4A.

The outer cover member 4A is formed in a tubular structure, and is formed of the same material as that of a flexible hose, operating unit, and so forth (a conduit in the present embodiment) of an endoscope, or a material exhibiting the same thermal insulating performance as that of these components, e.g., resin such as urethane, rubber, or the like, in the same way as with the outer cover member 4 of the aforementioned first embodiment.

The outer cover member 4A has openings formed at both ends thereof. Furthermore, a cap member 4a is detachably mounted at each of the openings through a predetermined watertight member. This provides a watertight connection between each of cap members 4a and the outer cover member 4A after mounting the cap members 4a to both ends of the outer cover member 4A. On the other hand, the outer cover member 4A allows the assembly formed of the conduit tubes 1 and the indicator casing 2 to be stored within the interior space thereof after the cap members 4a are detached from the outer cover member 4A.

On the other hand, each of the aforementioned cap members 4a has a through hole formed at approximately the center thereof. Such an arrangement allows the conduit tube 1 to be detachably inserted into the through hole through a predetermined watertight member. This ensures that the join between the conduit tube 1 and the cap member 4a is watertight. The other components are the same as those of the aforementioned first embodiment.

Description will be made below regarding the operation of the sterilization confirmation tester 10A having such a configuration according to the present embodiment for confirming effective sterilization.

First, the indicator 3 is installed within the indicator casing 2 of the sterilization confirmation tester 10A in the same way as with the first embodiment.

The indicator casing 2, which stores the indicator 3 therewithin and which has the conduit tubes 1 connected to both ends thereof, is introduced into the outer cover member 4A with the cap members 4a having been detached, so as to be stored therewithin.

The two cap members 4a, with proximal ends of the conduit tubes 1 having been inserted into the through holes of the two cap members 4a, are each attached so as to cover the openings formed at both ends of the outer cover member 4A.

The sterilization confirmation tester 10A in such a state is installed within a given sterilization apparatus (not shown), and sterilization treatment is executed according to a predetermined procedure. As a result, a sterilization agent such as ethylene oxide gas, steam, or the like, is introduced into the interior of the conduit tube 1 from the opening 1c. Then, the sterilization agent passes through the conduit tube 1, and acts upon the indicator 3 stored in the indicator casing 2.

After this sterilization step, the sterilization confirmation tester 10 is extracted from the sterilization apparatus, and confirmation of effective sterilization is made. Now, let us consider a case of employing a biological indicator as the indicator 3. In this case, first, the cap members 4a are detached, and the assembly formed of the conduit tubes 1 and the indicator casing 2 is extracted from the outer cover member 4A in a sterile environment.

Subsequently, the indicator 3 is extracted from the indicator storage cylinder 2b of the indicator casing 2 in this sterile environment, and is introduced into a predetermined culture medium. After the culturing step, effective sterilization is confirmed based upon whether or not bacteria appear on the culture medium.

On the other hand, let us consider a case of employing a chemical indicator as the indicator 3. In this case, after the extraction of the assembly formed of the conduit tubes 1 and the indicator casing 2 from the outer cover member 4A, the indicator 3 is extracted from the indicator storage cylinder 2b of the indicator casing 2, in the same way. Then, effective sterilization is confirmed by checking for the change in color of the indicator 3. Note that an arrangement in which the indicator storage cylinder 2b of the indicator casing 2 is formed of transparent resin has the advantage of allowing the change in color of the indicator 3 to be checked from the outside of the indicator storage cylinder 2b of the indicator casing 2 without a step for extracting the indicator 3, thereby effecting confirmation of effective sterilization.

As described above, the aforementioned second embodiment offers the same advantages as those of the first embodiment described above.

Note that the configuration of the outer cover member 4A of the sterilization confirmation tester 10A according to the aforementioned second embodiment is not restricted to such an arrangement described above. For example, an arrangement may be made in which the outer cover member 4A has a connection portion at a certain position thereof which allows the outer cover member 4A to be divided into two parts and which allows these two parts to be connected with each other in a watertight manner so as to form the outer cover member 4A. Such an arrangement allows the interior space within the outer cover member 4A to be opened and closed as desired. With such an arrangement, the aforementioned connection portion needs to be formed with a watertight structure.

Such an arrangement has the advantage of allowing the indicator 3 stored within the indicator casing 2 to be extracted more rapidly after the sterilization, by dividing the outer cover member 4A at the connection portion.

Third Embodiment

Figure 5:
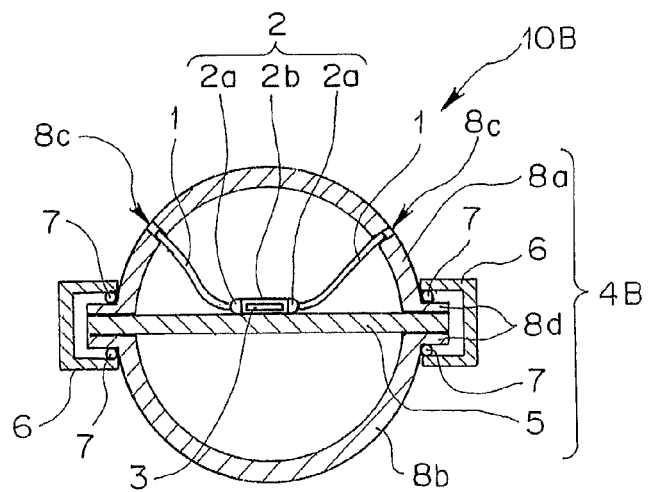
FIG. 5 is a side cross-sectional view which shows the schematic configuration of a sterilization confirmation tester according to a third embodiment of the present invention.
Figure 6:
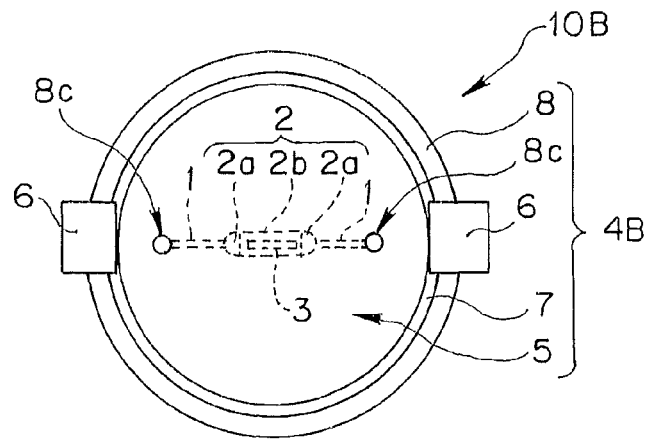
FIG. 6 is a top view which shows the schematic configuration of the sterilization confirmation tester shown in FIG. 5, when viewed from the top side.

FIG. 5 and FIG. 6 are diagrams which show a third embodiment of the present invention. Of these, FIG. 5 is a side cross-sectional view which shows the schematic configuration of a sterilization confirmation tester (corresponding to a conduit) according to the present embodiment. FIG. 6 is a top view which shows the schematic configuration of the sterilization confirmation tester shown in FIG. 5, when viewed from the top side.

The third embodiment has generally the same configuration as those of the aforementioned first and second embodiments, except for the outer cover member. Accordingly, the same components as those of the aforementioned first and second embodiments are denoted by the same reference numerals, detailed description thereof will be omitted, and description will be made below regarding only the different components.

As shown in FIG. 5 and FIG. 6, a sterilization confirmation tester 10B according to the present embodiment comprises the two conduit tubes 1, the indicator casing 2, the indicator 3, and an outer cover member 4B. Of these, the conduit tubes 1, the indicator casing 2, and the indicator 3 are the same as those of the aforementioned first and second embodiments.

The outer cover member 4B according to the present embodiment has a configuration which allows an assembly formed of the indicator casing 2 storing the indicator 3 and the two conduit tubes 1 to be detachably stored therewithin, as shown in FIG. 5, in the same way as with the aforementioned second embodiment. Accordingly, as shown in FIG. 5, the components corresponding to the conduit of an endoscope, i.e., the two conduit tubes 1 are enclosed within the outer cover member 4B.

The aforementioned outer cover member 4B comprises: two hemispherical shells 8a and 8b each of which has a flange 8d formed at the perimeter thereof; two fasteners 6 for fastening and fixing the two shells 8a and 8b via the flanges 8d of the two shells 8a and 8b; two O-rings 7 which are watertight members, one of which is introduced between the one fastener 6 and shell 8a and the other one of which is introduced between the other fastener 6 and the shell 8b, thereby providing a watertight seal between the one fastener 6 and the shell 8a and between the other fastener 6 and the shell 8b; a sheet 5 for mounting an assembly formed of the aforementioned conduit tubes 1 and the indicator casing 2 within the outer cover member 4B; and so forth.

The two shells 8a and 8b are formed of the same material as that of a flexible hose, operating unit, and so forth (which correspond to the conduit as described in the present embodiment) of an endoscope, or a material exhibiting the same thermal insulating performance as that of these components, e.g., resin such as urethane, rubber, or the like, in the same way as with the outer cover members 4 and 4A according to the aforementioned first and second embodiments.

Of these shells, the shell 8a has two through holes 8c formed at predetermined position on the outer face thereof. The through holes 8c allow the proximal ends of the two conduit tubes 1 connected to the indicator casing 2 stored within the outer cover member 4B to be detachably inserted thereinto through predetermined watertight members (not shown). Such a state provides a watertight seal between the conduit tube 1 and the through hole 8c.

With such an arrangement, the aforementioned two shells 8a and 8b are assembled into an approximately spherical structure with the sheet 5 interposed between the opposing flanges 8d. In this state, these flanges 8d are pressed to correspond to each other by the fasteners 6 with the O-rings 7 introduced therebetween, thereby ensuring that the interior space within the outer cover member 4B is watertight.

Each of the fasteners 6 is formed in a channel-shaped (C-shaped) cross-section and is formed of an elastic member. The fasteners 6 are provided for fastening the flanges 8d of the two shells 8a and 8b, thereby ensuring that the interior space within the aforementioned outer cover member 4B is watertight, as described above. With such an arrangement, the shells 8a and 8b are fastened and fixed by the fasteners 6 at a minimum of two positions on the perimeter of each flange 8d. Accordingly, at least two fasteners 6 are provided. The other components are the same as those of the aforementioned first and second embodiments.

Description will be made below regarding the operation of the sterilization confirmation tester 10B having such a configuration according to the present invention for confirming effective sterilization.

First, the indicator 3 is installed within the indicator casing 2 of the sterilization confirmation tester 10B in the same way as with the first and second embodiments.

The proximal ends of the conduit tubes 1 connected to both ends of the indicator casing 2 within which the indicator 3 has been installed are each inserted into the through holes 8c formed on the shell 8a.

Next, the two shells 8a and 8b are joined to each other with the sheet 5 introduced therebetween. Furthermore, the shells 8a and 8b are fastened and fixed by the fasteners 6 at predetermined position (two positions) on the flanges 8d of the shells 8a and 8b with the O-rings 7 introduced therebetween. Thus, the assembly formed of the conduit tubes 1 and the indicator casing 2 is stored within the outer cover member 4B. This ensures that the interior of the outer cover member 4B is watertight.

The sterilization confirmation tester 10B in such a state is installed within a given sterilization apparatus (not shown), and sterilization treatment is executed according to a predetermined procedure. As a result, a sterilization agent such as ethylene oxide gas, steam, or the like, is introduced into the interior of the indicator casing 2 from the through hole 8c formed on the shell 8a through the conduit tube 1. Then, the sterilization agent passes through the conduit tube 1, and acts upon the indicator 3 stored in the indicator casing 2.

After this sterilization step, the sterilization confirmation tester 10B is extracted from the sterilization apparatus, and confirmation of effective sterilization is made. Now, let us consider a case of employing a biological indicator as the indicator 3. In this case, first, the fasteners 6 are detached so as to separate the shells 8a and 8b from one another, and the assembly formed of the conduit tubes 1 and the indicator casing 2 is extracted from the interior of the outer cover member 4B in a sterile environment.

Subsequently, the indicator 3 is extracted from the indicator storage cylinder 2b of the indicator casing 2 in this sterile environment, and is introduced into a predetermined culture medium. After the culturing step, effective sterilization is confirmed based upon whether or not bacteria appear on the culture medium.

On the other hand, let us consider a case of employing a chemical indicator as the indicator 3. In this case, after the extraction of the assembly formed of the conduit tubes 1 and the indicator casing 2 from the outer cover member 4B, the indicator 3 is extracted from the indicator storage cylinder 2b of the indicator casing 2, in the same way. Then, effective sterilization is confirmed by checking for the change in color of the indicator 3. Note that an arrangement in which the indicator storage cylinder 2b of the indicator casing 2 is formed of transparent resin has the advantage of allowing the change in color of the indicator 3 to be checked from the outside of the indicator storage cylinder 2b of the indicator casing 2 without a step for extracting the indicator 3, thereby effecting confirmation of effective sterilization.

As described above, the aforementioned third embodiment offers the same advantages as that of the first and second embodiments described above.

Description has been made regarding an arrangement in which the spherical shells 8a and 8b are assembled into the approximately spherical outer cover member 4B. The present invention is not restricted to such an arrangement. Also, an arrangement may be made as described below.

Fourth Embodiment

Figure 7:
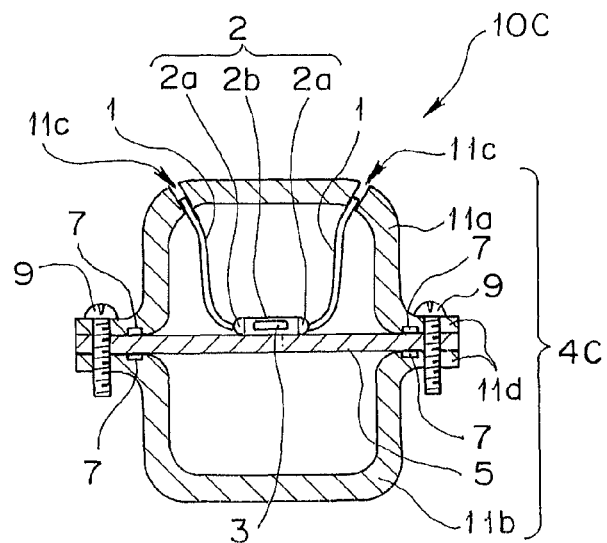
FIG. 7 is a side cross-sectional view which shows the schematic configuration of a sterilization confirmation tester according to a fourth embodiment of the present invention.
Figure 8:
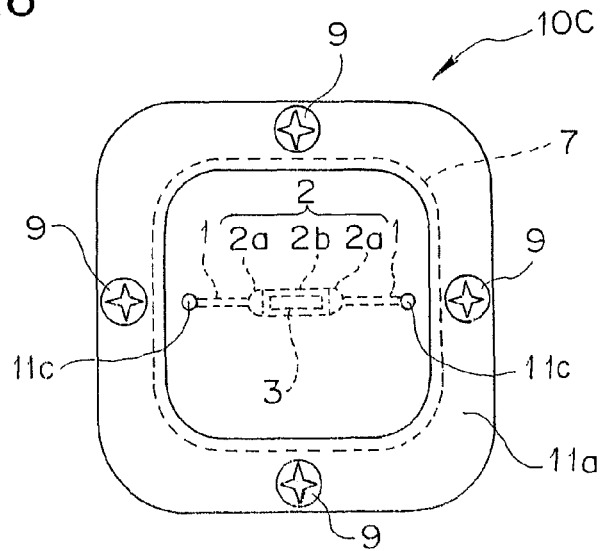
FIG. 8 is a top view which shows the schematic configuration of the sterilization confirmation tester shown in FIG. 7, when viewed from the top side.

FIG. 7 and FIG. 8 are diagrams which show a fourth embodiment of the present invention. Of these, FIG. 7 is a side cross-sectional view which shows the schematic configuration of a sterilization confirmation tester (corresponding to a conduit) according to the present embodiment. FIG. 8 is a top view which shows the schematic configuration of the sterilization confirmation tester shown in FIG. 7, when viewed from the top side.

The fourth embodiment has generally the same configuration as that of the aforementioned third embodiment, except for the structure of the outer cover member and the fasteners thereof. Accordingly, the same components as those of the aforementioned third embodiment are denoted by the same reference numerals, detailed description thereof will be omitted, and description will be made below regarding only the different components.

As shown in FIG. 7 and FIG. 8, a sterilization confirmation tester 10C according to the present embodiment comprises the two conduit tubes 1, the indicator casing 2, the indicator 3, and an outer cover member 4C. Of these, the conduit tubes 1, the indicator casing 2, and the indicator 3 are the same as those of the aforementioned first through third embodiments.

The outer cover member 4C according to the present embodiment has a configuration which allows an assembly formed of the indicator casing 2, storing the indicator 3, and the two conduit tubes 1 to be detachably stored therewithin, as shown in FIG. 7, in the same way as with the aforementioned second and third embodiment. Accordingly, as shown in FIG. 7, the components corresponding to the conduit of an endoscope, i.e., the two conduit tubes 1 are enclosed within the outer cover member 4C.

The aforementioned outer cover member 4C comprises: two box-shaped shells 11a and 11b each of which has an opening on one side thereof and a flange 11d formed around the perimeter of the opening; two bolts 9 which are fasteners for fastening and fixing the flanges 11d of the two shells 11a and 11b; the sheet 5, which is interposed between the aforementioned two shells 11a and 11b, for mounting an assembly formed of the aforementioned conduit tubes 1 and the indicator casing 2 within the outer cover member 4C; the two O-rings 7 which are watertight members, one of which is introduced between the aforementioned sheet 5 and the shell 11a and the other one of which is introduced between the sheet 5 and the shell 11b, thereby providing a watertight seal between the aforementioned sheet 5 and the shell 11a and between the sheet 5 and the shell 11b; and so forth.

The two shells 11a and 11b are formed of the same material as that of a flexible hose, operating unit, and so forth (which correspond to the conduit as described in the present embodiment) of an endoscope for example, or a material exhibiting the same thermal insulating performance as that of these components, e.g., resin such as urethane, rubber, or the like, in the same way as with the outer cover members 4, 4A, and 4B according to the aforementioned first through third embodiments.

Of these shells, the shell 11a has two through holes 11c formed at predetermined position on the outer face thereof. The through holes 11c allow the proximal ends of the two conduit tubes 1 connected to the indicator casing 2 stored within the outer cover member 4C to be detachably inserted thereinto via predetermined watertight members (not shown). Such a state provides a watertight seal between the conduit tube 1 and the through hole 11c.

With such an arrangement, the aforementioned two shells 11a and 11b are assembled into an approximately box-shaped structure with the sheet 5 interposed between the opposing flanges 11d. In this state, these flanges 11d are pressed into contact with each other by the bolts 9 with the O-rings 7 introduced therebetween, thereby ensuring that the interior space within the outer cover member 4C is watertight.

With the present embodiment, there are at least two (preferably four) fastening/fixing portions at the perimeter of the flange 11d as shown in FIG. 8. Accordingly, at least two (or four) bolts 9 are provided. The other components are the same as those of the aforementioned first and second embodiments.

Description will be made below regarding the operation of the sterilization confirmation tester 10C having such a configuration according to the present embodiment for confirming effective sterilization.

First, the indicator 3 is installed within the indicator casing 2 of the sterilization confirmation tester 10C in the same way as with the first through third embodiments.

The proximal ends of the conduit tubes 1 connected to both ends of the indicator casing 2, within which the indicator 3 has been installed, are each inserted into the through holes 11c formed on the shell 11a.

Next, the two shells 11a and 11b are joined to each other with the sheet 5 introduced therebetween. Furthermore, the shells 11a and 11b are fastened by the bolts 9 at predetermined position (four positions) on the flanges 11d of the shells 11a and 11b with the O-rings 7 introduced therebetween. Thus, the assembly formed of the conduit tubes 1 and the indicator casing 2 is stored within the outer cover member 4C. This ensures that the interior of the outer cover member 4C is watertight.

The sterilization confirmation tester 10C in such a state is installed within a given sterilization apparatus (not shown), and sterilization treatment is executed according to a predetermined procedure. As a result, a sterilization agent such as ethylene oxide gas, steam, or the like, is introduced into the interior of the indicator casing 2 from the through hole 11c formed on the shell 11a through the conduit tube 1. Then, the sterilization agent passes through the conduit tube 1, and acts upon the indicator 3 stored in the indicator casing 2.

After this sterilization step, the sterilization confirmation tester 10C is extracted from the sterilization apparatus, and confirmation of effective sterilization is made. Now, let us consider a case of employing a biological indicator as the indicator 3. In this case, first, the bolts 9 are detached so as to separate the shells 11a and 11b from one another, and the assembly formed of the conduit tubes 1 and the indicator casing 2 is extracted from the interior of the outer cover member 4C in a sterile environment.

Subsequently, the indicator 3 is extracted from the indicator storage cylinder 2b of the indicator casing 2 in this sterile environment, and is introduced into a predetermined culture medium. After the culturing step, effective sterilization is confirmed based upon whether or not bacteria appear on the culture medium.

On the other hand, let us consider a case of employing a chemical indicator as the indicator 3. In this case, after the extraction of the assembly formed of the conduit tubes 1 and the indicator casing 2 from the outer cover member 4C, the indicator 3 is extracted from the indicator storage cylinder 2b of the indicator casing 2, in the same way. Then, effective sterilization is confirmed by checking for the change in color of the indicator 3. Note that an arrangement in which the indicator storage cylinder 2b of the indicator casing 2 is formed of transparent resin has the advantage of allowing the change in color of the indicator 3 to be checked from the outside of the indicator storage cylinder 2b of the indicator casing 2 without a step for extracting the indicator 3, thereby effecting confirmation of effective sterilization.

As described above, the aforementioned fourth embodiment offers the same advantages as those of the first through third embodiments described above.

Note that the sheet 5 according to the aforementioned third and fourth embodiments may be formed in an approximately circular shape, for example. Also, the sheet 5 may be formed in the shape of a square, rectangle, triangle, or the like. Also, the sheet 5 may be formed in an easily usable shape as necessary.

The sterilization confirmation testers (10A, 10A, 10B, 10C), which are exemplary arrangements according to the aforementioned first through fourth embodiments, are formed in a shape corresponding to the conduit of an endoscope (see FIG. 1 through FIG. 8).

A sterilization confirmation tester according to an embodiment described below is an arrangement which corresponds to at least one of the components forming a endoscope, e.g., an arrangement which corresponds to a structure for mounting the operating lever of an operating unit to an operating main unit of the endoscope.

Fifth Embodiment

Figure 9:
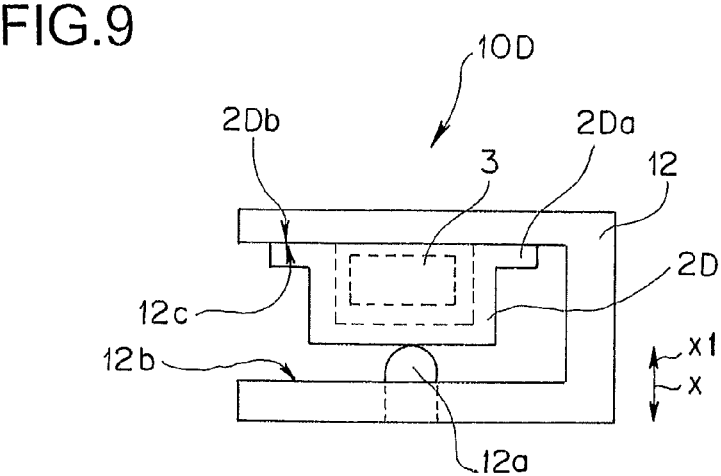
FIG. 9 is a side view which shows the schematic configuration of a sterilization confirmation tester according to a fifth embodiment of the present invention.
Figure 10:
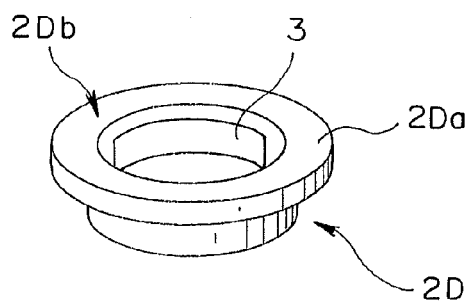
FIG. 10 is a perspective view which shows only an indicator casing which is one of the components of the sterilization confirmation tester shown in FIG. 9.

FIG. 9 and FIG. 10 are diagrams which show a fifth embodiment of the present invention. Of these, FIG. 9 is a side view which shows the schematic configuration of a sterilization confirmation tester (corresponding to an operating unit) according to the present embodiment. FIG. 10 is a perspective view which shows only an indicator casing which is one of the components of the sterilization confirmation tester according to the present embodiment.

A sterilization confirmation tester 10D according to the present embodiment comprises: an indicator casing 2D for installing the indicator 3 having the same structure as that employed in the aforementioned first through fourth embodiments; and a holder 12 for holding the indicator casing 2D.

A sterilization confirmation tester 10D according to the present embodiment is for confirming effective sterilization of a sterilization apparatus. The sterilization confirmation tester 10D has a structure which corresponds to at least one of the components of an endoscope, i.e., which corresponds to the contact faces of a main unit member and a lever member of the operating unit of the endoscope.

The indicator casing 2D is formed in a cylindrical shape having an opening at one end thereof, and has a flange 2Da around the perimeter of the opening. The indicator casing 2D is formed of a material equivalent to that of the operating unit and so forth of an endoscope, e.g., resin such as polysulfone resin or the like, metal such as stainless steel or the like, or the like. Furthermore, the indicator casing 2D is configured so as to allow the indicator 3 to be installed at a predetermined position on the inner wall of the indicator casing 2D.

The holder 12 has a channel-shaped (C-shaped) cross-section, and is formed of the same material as that of the aforementioned indicator casing 2D, i.e., the material equivalent to that of the operating unit and so forth of an endoscope, e.g., resin such as polysulfone resin or the like, metal such as stainless steel or the like, or the like.

Furthermore, a protrusion 12a is provided on the wall face 12a, which is an inner face of the bottom wall of the holder 12, so as to protrude toward the opposite wall face 12c. The protrusion 12a is formed of an elastic member having such a height that it provides a gap between the top of the protrusion 12a and the wall face 12c which is somewhat smaller than the height of the indicator casing 2D. Such an arrangement allows the indicator casing 2D to be held with the outer face of the bottom thereof being pressed by the protrusion 12a in the direction X1 indicated by the arrow in FIG. 9. At this stage, the indicator casing 2D is situated in a space between the opposing wall face 12c and the top of the protrusion 12a of the holder 12 as shown in FIG. 9. In this state, the indicator casing 2D is held with the face 2Db of the flange 2Da thereof being in contact with the opposing wall face 12c of the holder 12.

The contact faces of the indicator casing 2D and the holder 12 are formed with a surface roughness equivalent to that of the contact faces where a lever member, which is a component of the operating lever of the operating unit of an endoscope, and a main unit member, which is a component of the endoscope main unit, are in contact with each other.

Description will be made below regarding the operation of the sterilization confirmation tester 10D having such a configuration according to the present embodiment for confirming effective sterilization.

First, the indicator casing 2 storing the indicator 3 is mounted at a predetermined position of the holder 12, i.e., in a space between the opposing wall face 12c and the top of the protrusion 12a of the holder 12 as shown in FIG. 9.

Next, the sterilization confirmation tester 10D is installed within a given sterilization apparatus (not shown), and sterilization treatment is executed. As a result, a sterilization agent such as ethylene oxide gas, steam, or the like, is introduced into the interior of the indicator casing 2D from a slight gap in the contact portion where the opposing wall face 12c of the holder 12 and the face 2Db of the flange 2Da of the indicator casing 2D are pressed into contact therewith. Then, the sterilization agent acts upon the indicator 3 stored in the indicator casing 2.

After this sterilization step, the sterilization confirmation tester 10D is extracted from the sterilization apparatus, and confirmation of effective sterilization is made. Now, let us consider a case of employing a biological indicator as the indicator 3. In this case, first, the indicator casing 2D is extracted from the holder 12 in a sterile environment.

Subsequently, the indicator 3 is extracted from the indicator casing 2 in this sterile environment, and is introduced into a predetermined culture medium. After the culturing step, effective sterilization is confirmed based upon whether or not bacteria appear on the culture medium.

On the other hand, let us consider a case of employing a chemical indicator as the indicator 3. In this case, after the extraction of the indicator casing 2D from the holder 12 in the same way, the change in color of the indicator 3 is checked for through the opening of the indicator casing 2D, thereby making confirmation of sterilization results.

With the above fifth embodiment as described above, the sterilization confirmation tester 10D is formed with a structure which is a simulation of a gap which typically occurs between the operating lever of the operating unit and the endoscope main unit of the endoscope and so forth. This provides confirmation of effective sterilization at a corresponding portion of an endoscope with high reliability.

The sterilization confirmation tester 10D can also be applied to other cases, as well as a case described in the aforementioned fifth embodiment. Now, let us consider a case in which the effective sterilization of a treatment tool (not shown) or the like used together with the endoscope, for example, is confirmed using the sterilization confirmation tester 10D according to the present embodiment. In this case, this confirmation of effective sterilization can be made simply by using the holder 12 and the indicator casing 2D having the contact faces with a surface roughness equivalent to that of the contact faces of this treatment tool.

By the way, description has been made in the above first through fifth embodiments regarding exemplary arrangements of the sterilization confirmation tester which is a simulation of a predetermined portion of an endoscope. Such an arrangement requires that confirmation operations (sterilization confirmation test), including installation of each sterilization confirmation tester and confirmation thereof, should be performed for each sterilization confirmation tester.

Accordingly, an arrangement which has a function of allowing sterilization and subsequent confirmation of effective sterilization to be performed all at the same time and with respect to various kinds of sterilization confirmation testers corresponding to various portions of an endoscope, would be very convenient. Next, description will be made regarding a test pack having a function of storing multiple sterilization confirmation testers having structures corresponding to two different components of an endoscope according to an embodiment.

Sixth Embodiment

Figure 11:
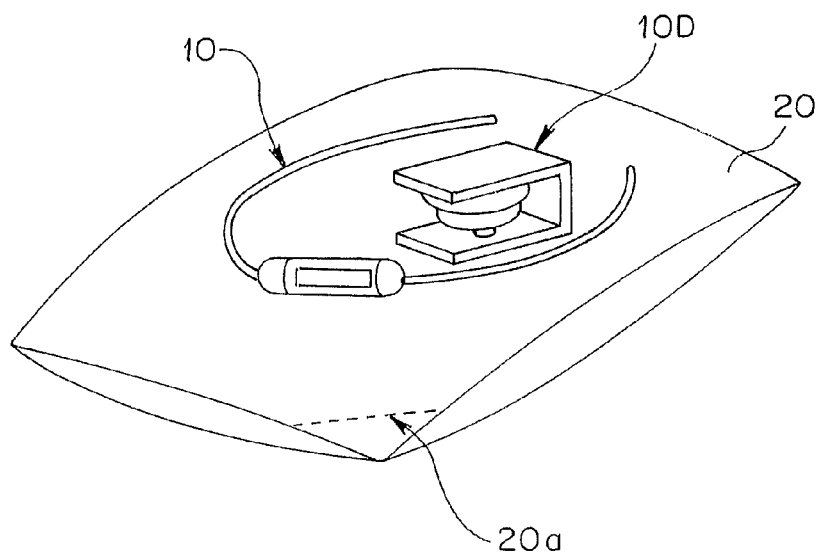
FIG. 11 is a diagram which shows a sixth embodiment of the present invention, and is an external view which shows a test pack storing two sterilization confirmation testers having structures corresponding to two different components of an endoscope.

FIG. 11 is a diagram which shows a sixth embodiment of the present invention, and is an external view which shows a test pack storing two sterilization confirmation testers having structures corresponding to two different components of an endoscope.

A test pack 20 according to the present embodiment is formed in an approximately bag-like shape for storing multiple sterilization confirmation testers. For example, the test pack 20 is formed of a sterilization peel pack or the like, for example. Here, the peel pack as used here represents a packaging member having a function of allowing air such as vapor or the like to pass therethrough while preventing liquid and bacteria from passing therethrough, which has been widely employed as a conventional packaging member in the field of medical devices.

Furthermore, a tearable portion 20a, formed in the shape of a perforated line for example, is provided at one of the four corners of the test pack 20. The tearable portion 20a is provided for facilitating opening of the test pack 20.

The test pack 20 is configured so as to allow at least two sterilization confirmation testers to be stored as shown in FIG. 11. With such an arrangement, each sterilization confirmation tester, which is to be stored in this test pack 20, has a structure corresponding to at least one of the components of the endoscope.

Specifically, FIG. 11 shows a state in which the aforementioned test pack 20 simultaneously stores the sterilization confirmation tester 10 according to the aforementioned first embodiment, i.e., a tester corresponding to a conduit of the endoscope, and the sterilization confirmation tester 10D according to the aforementioned fifth embodiment, i.e., a tester which is a simulation of the gap between the contact faces of the operating lever of the operating unit of the endoscope and the endoscope main unit.

Description will be made regarding the operations including simultaneous sterilization treatment for multiple sterilization confirmation testers and subsequent confirmation of effective sterilization, using the test pack 20 having such a configuration. First, the two sterilization confirmation testers 10 and 10D having different structures as described above are stored within the test pack 20, and the test pack 20 is sealed.

This test pack 20 is installed within a given sterilization apparatus (not shown), and sterilization treatment is executed. As a result, a sterilization agent such as ethylene oxide gas, steam, or the like, is introduced into the interior of the test pack 20. Then, the sterilization agent acts upon the indicators 3 stored in the indicator casings 2 and 2D of the sterilization confirmation testers 10 and 10D.

After this sterilization step, the sterilization confirmation testers 10 and 10D are extracted from the sterilization apparatus, and confirmation of effective sterilization is made. Now, let us consider a case of employing biological indicators as the indicators 3. In this case, first, the test pack 20 is opened by being torn along the tearable portion 20a of the test pack 20, the sterilization confirmation testers 10 and 10D are extracted from the test pack 20, and the indicators 3 are extracted therefrom, in a sterile environment.

Subsequently, each indicator 3 thus extracted is introduced into a predetermined culture medium. After the culturing step, effective sterilization is confirmed based upon whether or not bacteria appear on the culture medium.

On the other hand, let us consider a case of employing chemical indicators as the indicators 3. In this case, each indicator 3 is extracted from the indicator storage cylinder 2b of the indicator casing 2, and effective sterilization is confirmed by checking for the change in color of the indicator 3. Note that an arrangement in which the indicator storage cylinder 2b of the indicator casing 2 is formed of transparent resin has the advantage of allowing the change in color of the indicator 3 of the sterilization confirmation tester 10 to be checked from the outside without a step for extracting the indicator 3, thereby effecting confirmation of effective sterilization. In particular, for the indicator 3 of the sterilization confirmation tester 10, such an arrangement provides the advantage of allowing the confirmation of effective sterilization to be made without opening the test pack 20. On the other hand, with regard to the indicator 3 of the sterilization confirmation tester 10D, after the extraction of the sterilization confirmation tester 10D from the opened test pack 20, the indicator casing 2D is extracted from the holder 12. Then, the change in color of the indicator 3 is checked for through the opening of the indicator casing 2D, thereby confirming effective sterilization.

With the above sixth embodiment as described above, the sterilization treatment and the subsequent confirmation of effective sterilization can be performed simultaneously for multiple different testers. This means that there is no need to perform a series of confirmation operations for each tester, thereby improving the efficiency of the confirmation operations.

And now, description has been made regarding the indicator casing 2 according to the above first through fourth embodiments, which comprises the indicator storage cylinder 2b and the two caps 2a detachably provided to both ends thereof, as described above. Description will be made regarding the indicator casing 2 having another structure according to an embodiment, which is employed instead of the indicator casing 2 according to the above first through fourth embodiments.

Seventh Embodiment

Figure 12:
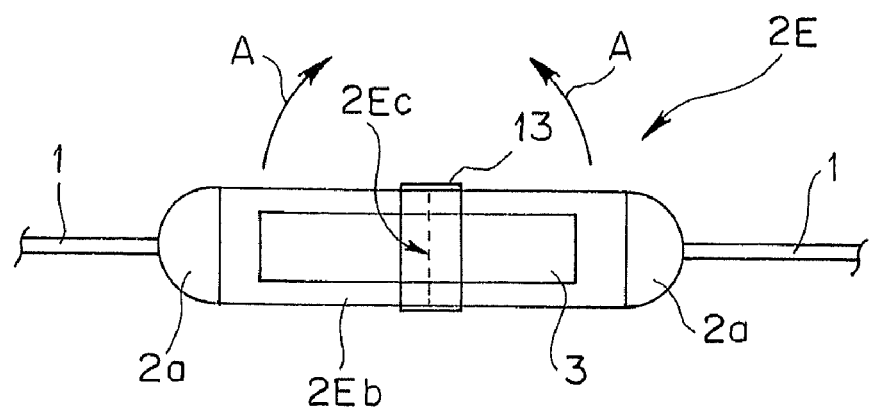
FIG. 12 is an external view of an indicator casing of a sterilization confirmation tester according to a seventh embodiment of the present invention.
Figure 13:
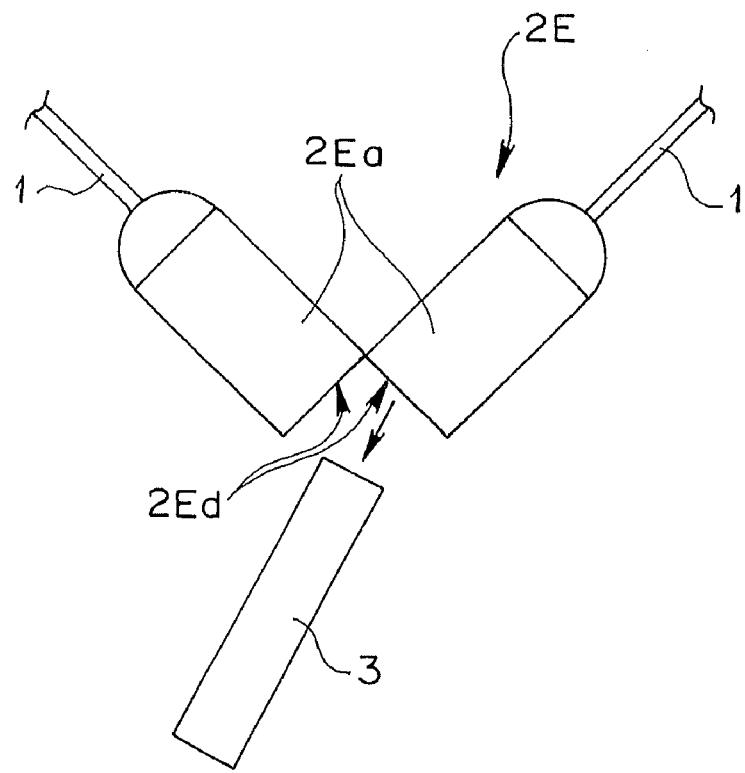
FIG. 13 is an external view which shows a state in which the indicator casing shown in FIG. 12 has been opened.

Specifically, FIG. 12 and FIG. 13 show a seventh embodiment according to the present invention. Of these, FIG. 12 is an external view of an indicator casing of a sterilization confirmation tester. On the other hand, FIG. 13 is an external view which shows a state in which the indicator casing shown in FIG. 12 has been opened.

An indicator casing 2E according to the present embodiment has generally the same configuration as that of the indicator casing 2 employed in the sterilization confirmation tester according to the aforementioned first through fourth embodiments, except that the structure of an indicator storage cylinder 2Eb is somewhat different. Accordingly, the same components as those of the aforementioned first through fourth embodiments are denoted by the same reference numerals, detailed description thereof will be omitted, and description will be made below regarding only the different components.

As shown in FIG. 12, the indicator casing 2E comprises the indicator storage cylinder 2Eb and the two caps 2a integrally provided to both ends thereof.

With such an arrangement, the proximal ends 1a of the two conduit tubes 1 are each detachably connected to the tip ends of the two caps 2a in a watertight manner.

Furthermore, each of the two caps 2a and the indicator storage cylinder 2Eb are integrally connected with each other in a watertight manner.

Furthermore, a separatable portion 2Ec, which is separating means, is formed at around the center of the indicator storage cylinder 2Eb, which allows the indicator storage cylinder 2Eb to be separated into two parts by simply applying a certain amount of force. The separatable portion 2Ec is provided at a desired position on the outer face of the indicator storage cylinder 2Eb in the form of a perforated line or the like, for example.

Accordingly, upon applying a predetermined, or greater, amount of force to the indicator storage cylinder 2Eb in the direction where the indicator storage cylinder 2Eb is to be bent with the separatable portion 2Ec as a fulcrum, i.e., in the direction A indicated by the arrow in FIG. 12, the indicator storage cylinder 2Eb comes to be separated along the separatable portion 2Ec, thereby forming an openings 2Ed (see FIG. 13), which allows the object stored within, such as the indicator 3 or the like to be extracted. That is to say, the indicator casing 2E includes the separatable portion 2Ec having a function of separating the indicator casing 2E into two parts so as to form openings upon receipt of a predetermined amount of force.

Furthermore, a watertight seal 13 is adhered to the separatable portion 2Ec, thereby ensuring that the indicator casing 2E is watertight. The other components are generally the same as those of the aforementioned first embodiment.

Description will be made below regarding the operations for confirmation of effective sterilization using the sterilization confirmation tester including the aforementioned indicator casing 2E having such a configuration.

First, the indicator 3 is installed within the indicator casing 2E. Then, the watertight seal 13 is adhered to the separatable portion 2Ec.

The sterilization confirmation tester including the aforementioned indicator casing 2E having such a configuration is installed within a given sterilization apparatus (not shown), and sterilization treatment is executed according to a predetermined procedure. As a result, a sterilization agent such as ethylene oxide gas, steam, or the like, is introduced into the interior of the conduit tube 1 from the opening thereof (1c, see FIG. 1). Then, the sterilization agent passes through the conduit tube 1, and acts upon the indicator 3 stored in the indicator casing 2E.

After this sterilization step, the sterilization confirmation tester is extracted from the sterilization apparatus, and confirmation of effective sterilization is made. Now, let us consider a case of employing a biological indicator as the indicator 3. In this case, first, force is applied to the indicator casing 2E with the separatable portion 2Ec as a fulcrum, in the direction A indicated by the arrow in FIG. 12 such that the indicator casing 2E is separated into two parts in a sterile environment as shown in FIG. 13. Subsequently, the indicator 3 is extracted from the indicator casing 2E through the opening 2Ed. Then, the indicator 3 is introduced into a predetermined culture medium. After the culturing step, effective sterilization is confirmed based upon whether or not bacteria appear on the culture medium.

In a case where the same confirmation test of the sterilization treatment is repeatedly performed, after a new indicator 3 is installed within the indicator casing 2E, a structure is formed with the openings 2Ed of the indicator storage cylinder 2Eb paired at the separatable portion 2Ec. Then, the watertight seal 13 is adhered to the separatable portion 2Ec. The subsequent procedure is the same as that described above.

Also, a chemical indicator may be employed as the indicator 3. In this case, an arrangement employing the transparent indicator storage cylinder 2Eb has the advantage of allowing the change in color of the indicator 3 to be checked without a step for extracting the indicator 3 from the indicator storage cylinder 2Eb, thereby effecting confirmation of effective sterilization. Note that the same confirmation test of the sterilization treatment may be repeatedly performed. In this case, first, the indicator storage cylinder 2Eb is separated into two parts at the separatable portion 2Ec, and a new indicator 3 is installed in the indicator storage cylinder 2Eb. Then, the watertight seal 13 is adhered to the separatable portion 2Ec. The subsequent operations are the same as described above.

With the aforementioned seventh embodiment as described above, the separatable portion 2Ec allows the indicator storage cylinder 2Eb to be separated into two parts simply by applying a predetermined amount of force to a predetermined portion of the indicator storage cylinder 2Eb of the indicator casing 2E in the direction where the indicator storage cylinder 2Eb is to be bent. This facilitates installation/ extraction of the indicator 3 into/from the indicator casing 2E, thereby reducing the operating time.

In a case where a biological indicator is employed as the indicator 3, the indicator 3 needs to be extracted from the interior of the indicator casing 2E in a sterile environment. The present embodiment enables the operation for extracting the indicator 3 to be executed in a simple and sure manner. This suppresses error in confirmation of effective sterilization, thereby improving the precision of the confirmation of effective sterilization.

Eighth Embodiment

And now, in a case where a biological indicator is employed as the indicator 3, the operations in a sterile environment for confirming effective sterilization are required.

Accordingly, an arrangement, which has a function of enabling the indicator 3 to be introduced into a predetermined culture medium in a sterile environment in a simple manner while allowing the user to remain in a space other than the sterilization environment, would be every convenient.

Figure 14:
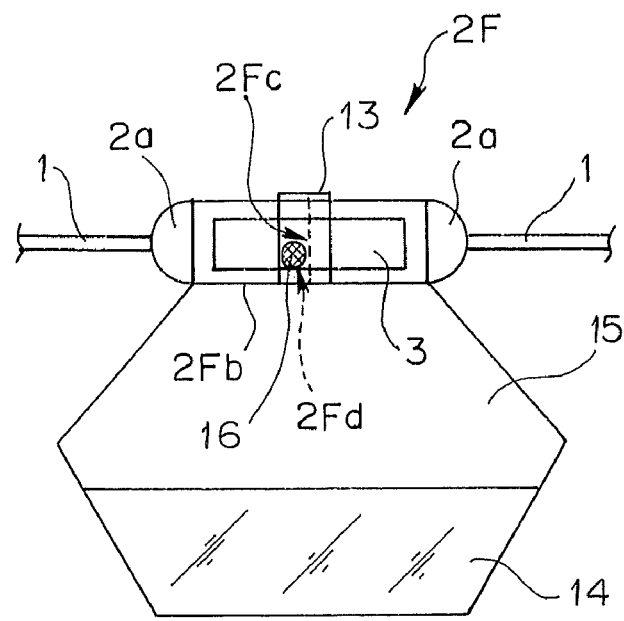
FIG. 14 is an external view of an indicator casing of a sterilization confirmation tester including a culture medium according to an eighth embodiment of the present invention.
Figure 15:
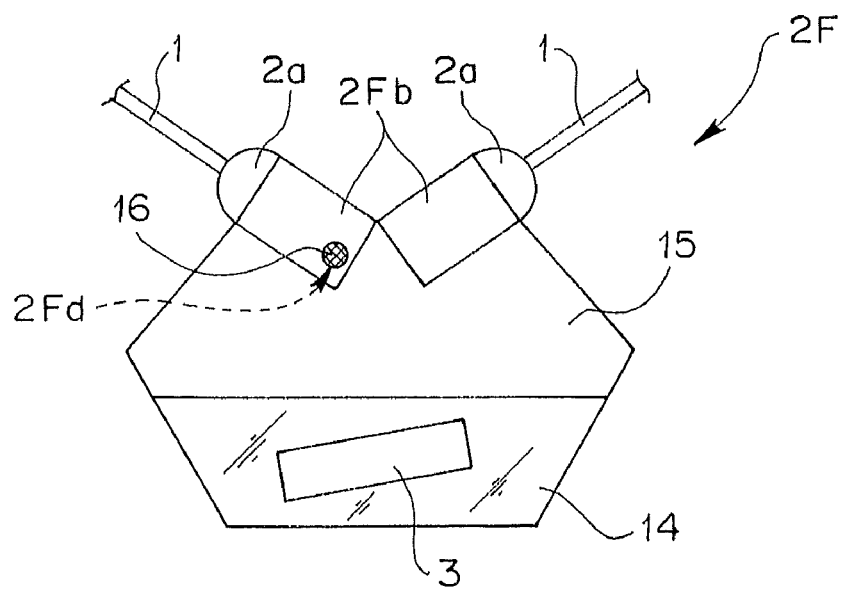
FIG. 15 is an external view which shows a state in which the indicator casing shown in FIG. 14 has been opened.

FIG. 14 and FIG. 15 show an eighth embodiment according to the present invention. Of these, FIG. 14 is an external view of an indicator casing of a sterilization confirmation tester including a culture medium. On the other hand, FIG. 15 is an external view which shows a state in which the indicator casing shown in FIG. 14 has been opened.

An indicator casing 2F according to the present embodiment has generally the same configuration as that of the indicator casing 2E employed in the sterilization confirmation tester according to the aforementioned seventh embodiment, except that the indicator casing 2F aseptically and integrally includes a culture medium used for a culturing step for a biological indicator employed as the indicator 3. Accordingly, the same components as those of the aforementioned seventh embodiment are denoted by the same reference numerals, detailed description thereof will be omitted, and description will be made below regarding only the different components.

As shown in FIG. 14, the indicator casing 2F comprises the indicator storage cylinder 2Fb, the two caps 2a integrally provided to both ends thereof, and a culture medium bag 15 including a culture medium 14.

Furthermore, a separatable portion 2Fc, which is separating means, is formed at around the center of the indicator storage cylinder 2Eb, which allows the indicator storage cylinder 2Eb to be separated into two parts simply by applying a certain amount of force, in the same way as with the aforementioned seventh embodiment. Furthermore, the watertight seal 13 is adhered to the separatable portion 2Fc, thereby ensuring that the interior thereof is watertight, in the same way as with the aforementioned seventh embodiment.

Furthermore, the indicator storage cylinder 2Fb integrally includes the aforementioned culture medium bag 15 in a watertight manner. The culture medium bag 15 is formed of a transparent resin film or the like, for example. Furthermore, the culture medium bag 15 is formed having a size margin which ensures that the culture medium bag 15 does not tear due to tension or the like even in the state shown in FIG. 15, i.e., in the state in which the indicator storage cylinder 2Fb has been separated into two parts at the separatable portion 2Fc. With such an arrangement, upon separating the indicator storage cylinder 2Fb into two parts, the culture medium bag 15 covers the portions where the indicator storage cylinder 2Fb has been opened, in a watertight manner, and provides a culture medium for the biological indicator, as described later. Note that the culture medium bag 15 may have a mechanism for activating the culture medium 14.

Furthermore, the indicator casing 2F has a vent hole 2Fd formed at a portion which is to be covered with the watertight seal 13, around the separatable portion 2Fc of the indicator storage cylinder 2Fb, thereby forming a communicating passage between the inside and the outside of the indicator storage cylinder 2Fb. Furthermore, a filter 16 is provided to the vent hole 2Fd, which allows only air to pass therethrough while preventing bacteria, dust, and the like which are present in the surrounding area from passing therethrough, for example. The other components are generally the same as those of the first embodiment described above.

Description will be made below regarding the operations for confirmation of effective sterilization using the sterilization confirmation tester including the aforementioned indicator casing 2F having such a configuration.

First, the indicator 3 is installed within the indicator casing 2F in the same way as with the aforementioned seventh embodiment. Then, the watertight seal 13 is adhered to the separatable portion 2Fc, thereby ensuring that the separatable portion 2Fc is watertight.

The sterilization confirmation tester including the aforementioned indicator casing 2F having such a configuration is installed within a given sterilization apparatus (not shown), and sterilization treatment is executed according to a predetermined procedure. As a result, a sterilization agent such as ethylene oxide gas, steam, or the like, is introduced into the interior of the conduit tube 1 from the opening thereof (1c, see FIG. 1). Then, the sterilization agent passes through the conduit tube 1, and acts upon the indicator 3 stored in the indicator casing 2F.

After this sterilization step, the sterilization confirmation tester is extracted from the sterilization apparatus, and confirmation of effective sterilization is made. With the present embodiment, a biological indicator is employed as the indicator 3. In this case in which a biological indicator is employed as the indicator 3, first, a predetermined amount of force is applied to a predetermined portion of the indicator storage cylinder 2Fb of the indicator casing 2F in the same way as with the aforementioned seventh embodiment. As a result, the indicator storage cylinder 2Fb is separated into two parts as shown in FIG. 15, whereupon the indicator 3 is introduced into the culture medium 14 through the opening.

Then, the watertight seal 13 is peeled off, whereupon the vent hole 2Fd is exposed. This allows air, which is necessary for culturing bacteria, to be introduced into the interior of the culture bag 15 through the conduit tube 1 and the vent hole 2Fd, while the indicator storage cylinder 2Fb remains closed.

The sterilization confirmation tester in this state is installed in an incubator or the like, and cultivation is performed at a constant temperature for a predetermined period of time. Subsequently, effective sterilization is confirmed based upon whether or not bacteria appear on the culture medium.

Specifically, in the event that a bacterial culture does not appear after the culturing, due to the absence of bacteria on the indicator 3 introduced into the culture medium 14 in the culture medium bag 15, determination is made that sterilization has been properly performed.

As described above, the aforementioned eighth embodiment allows the culturing treatment to be performed for a biological indicator after sterilization treatment in a simple manner without involving special operations in a sterile environment. This permits easier sterilization treatment. At the same time, this ensures that the indicator 3 is in a sterilization state at all times throughout the step in which the indicator 3 is introduced into the culture medium 14 without any particular need to be concerned about whether or not a sterilization environment is maintained. This eliminates a cause of error in confirmation of effective sterilization. Accordingly, this reduces the operating time and improves the precision of the confirmation.

The first through eighth embodiments described above provide a sterilization confirmation tester and a test pack, which are configured so as to correspond to a medical device having a particular structure such as an endoscope or the like, thereby allowing confirmation of effective sterilization to be made for the endoscope or the like in a sure and simple manner.

Ninth Embodiment

Figure 16:
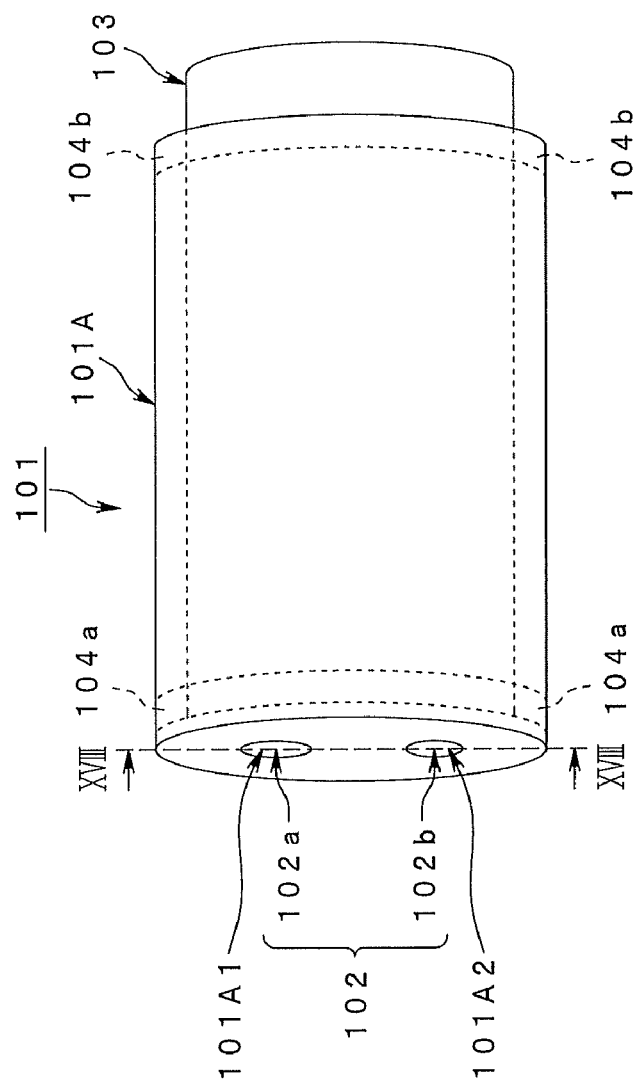
FIG. 16 is a perspective view which shows a schematic configuration of a sterilization confirmation tester according to a ninth embodiment of the present invention, at a basic length.
Figure 17:
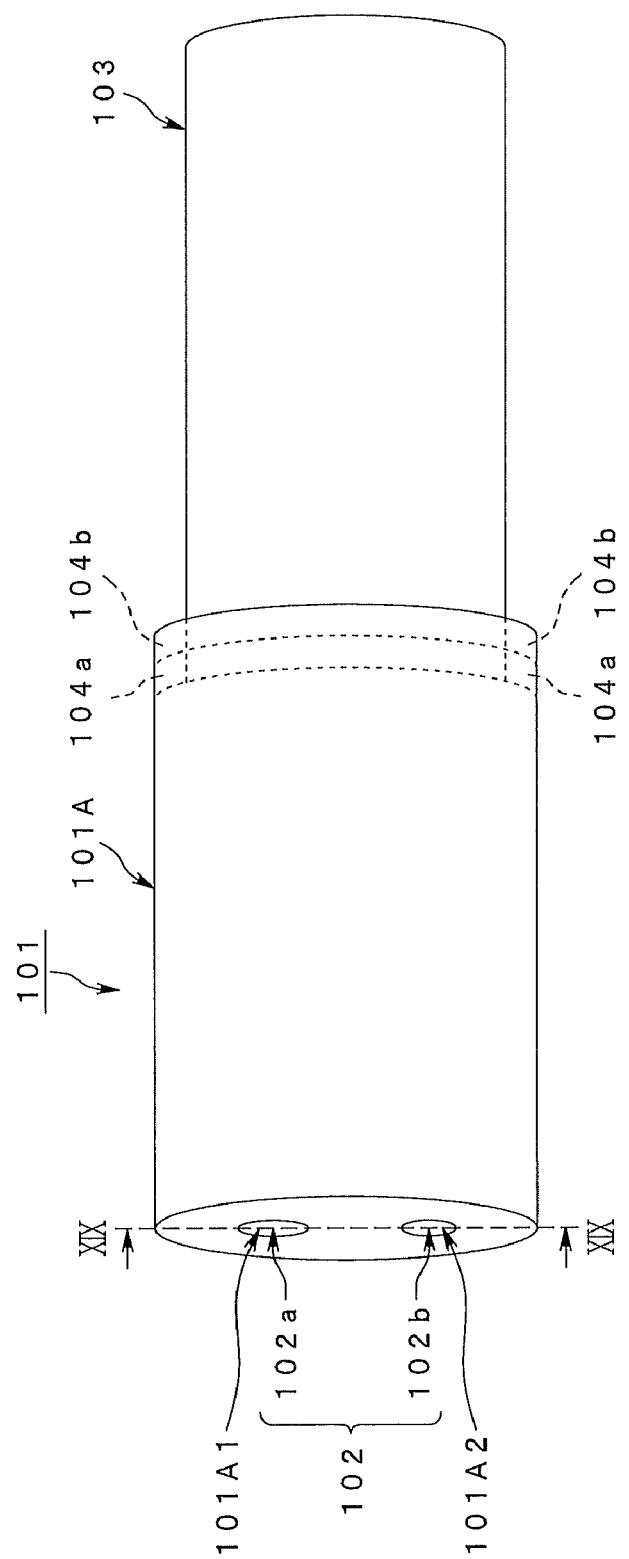
FIG. 17 is a perspective view which shows a schematic configuration of the sterilization confirmation tester according to the ninth embodiment of the present invention, with a length modified from the state shown in FIG. 16.
Figure 18:
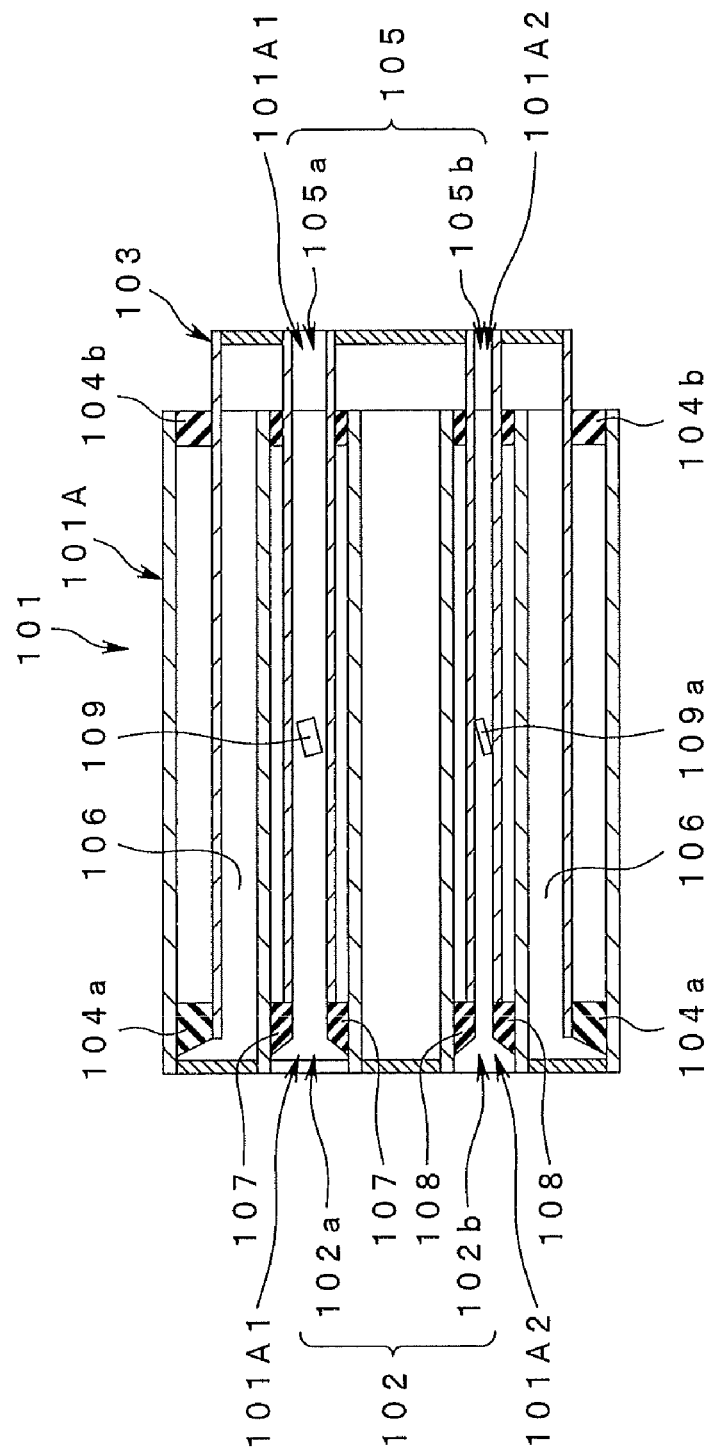
FIG. 18 is a cross-sectional view along line XVIII-XVIII in FIG. 16 showing the sterilization confirmation tester.
Figure 19:
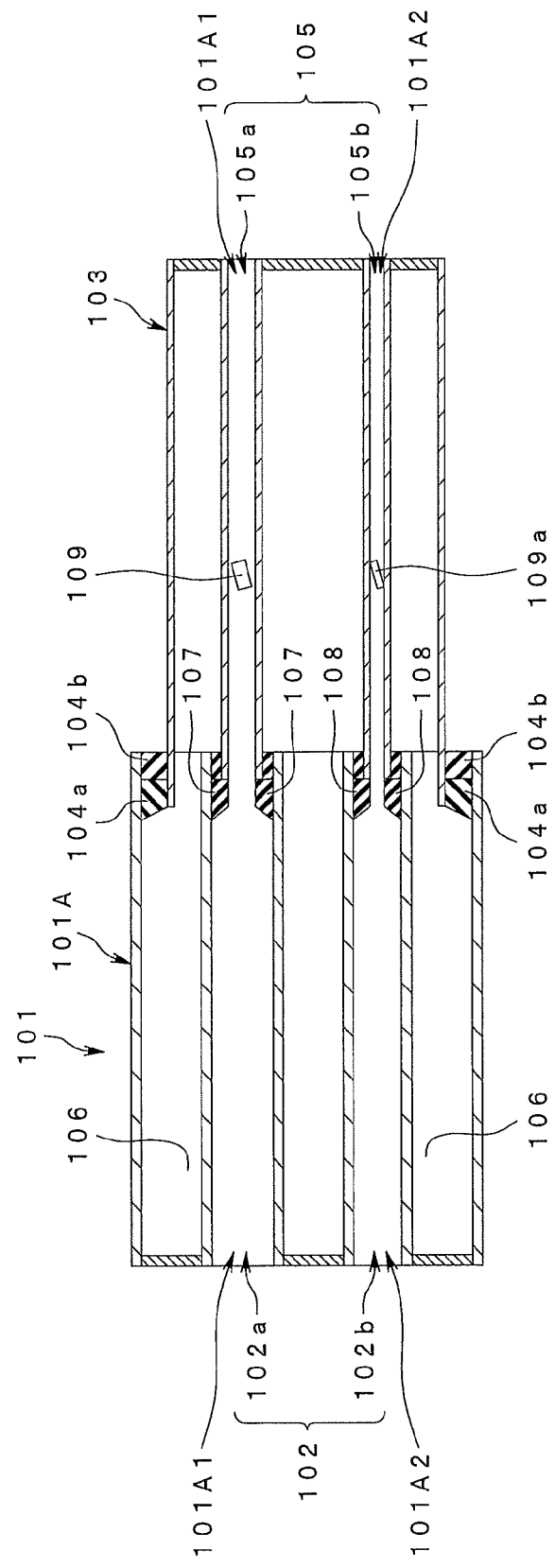
FIG. 19 is a cross-sectional view along line XIX-XIX in FIG. 17 showing the sterilization confirmation tester.

FIG. 16 through FIG. 19 show a sterilization confirmation tester according to a ninth embodiment of the present invention. FIG. 16 and FIG. 17 are perspective views which show the schematic configuration of the sterilization confirmation tester. FIG. 16 shows the sterilization confirmation tester at its a basic length. FIG. 17 shows the sterilization confirmation tester at a modified length. FIG. 18 and FIG. 19 are cross-sectional views along line XVIII-XVIII in FIG. 16 and line XIX-XIX in FIG. 17, respectively, each of which shows the sterilization confirmation tester. FIG. 18 shows the sterilization confirmation tester in a state corresponding to the state shown in FIG. 16. FIG. 19 shows the sterilization confirmation tester in a state corresponding to the state shown in FIG. 17.

As shown in FIG. 16, a sterilization confirmation tester 101 according to the present embodiment is configured so that it can be stored in a sterilization apparatus. The sterilization confirmation tester 101 includes two conduit simulation portions (first and second conduit simulation portions 101A1 and 101A2) having structures corresponding to the conduits of a medical device. With such an arrangement, the first and second conduit simulation portions 101A1 and 101A2 are configured such that the lengths thereof can be adjusted in the longitudinal direction.

Specifically, the aforementioned sterilization confirmation tester 101 includes a first and second conduit body 101A and 103 including the aforementioned first and second conduit simulation portions 101A1 and 101A2 therewithin. With such an arrangement, the second conduit body 103 is slidably mounted within the first conduit body 101A. Such an arrangement allows the lengths of the aforementioned first and second conduit simulation portions 101A1 and 101A2 to be adjusted in the longitudinal direction by sliding the second conduit body 103 relative to the first conduit body 101A.

As shown in FIG. 18, the aforementioned first conduit simulation portion 101A1 includes a conduit portion 102a included in the first conduit body 101A and a conduit portion 105a included in the second conduit body 103 as described below. On the other hand, the aforementioned second conduit simulation portion 101A2 includes a conduit portion 102b included in the first conduit body 101A and a conduit portion 105b included in the second conduit body 103 as described later.

Now, description will be made regarding the structures of the aforementioned first and second conduit bodies 101A and 103.

The aforementioned first conduit body 101A includes a conduit portion 102 which forms a part of the aforementioned first conduit simulation portion 101A1 and a part of the aforementioned second conduit simulation portion 101A2. The conduit portion 102 includes the two conduit portions 102a and 102b having different diameters, for example. In this case, one of these conduit portions, the conduit portion 102a corresponds to the aforementioned first conduit portion 101A1. The other conduit portion, i.e., the conduit portion 102b corresponds to the aforementioned second conduit simulation portion 101A2.

While description has been made in the present embodiment regarding an arrangement in which the aforementioned conduit portion 102 includes the conduit portions 102a and 102b having different diameters, the present invention is not restricted to such an arrangement. Also, an arrangement may be made in which the conduit portion 102 includes the conduit portions 102a and 102b having the same diameter. Also, an arrangement may be made in which the conduit portion bifurcates. Also, the conduit portion 102 may include only a single conduit portion, or may include multiple (two or more) conduit portions.

On the other hand, the aforementioned second conduit body 103 is slidably mounted within the aforementioned first conduit body 101A so as to allow the lengths of the conduit simulation portions to be adjusted as desired in the longitudinal direction. Furthermore, a ring-shaped elastic member 104b is attached to the inner face of the first conduit body 101A on the base end side which is in contact with the outer face of the second conduit body 103. The elastic member 104b maintains a watertight seal between the inner face of the first conduit body 101A and the outer face of the second conduit body 103 while allowing the second conduit body 103 to be moved in a sliding manner.

Accordingly, such an arrangement allows the aforementioned first conduit body 101A or the aforementioned second conduit body 103 to be moved in a sliding manner from the state shown in FIG. 16 to the state shown in FIG. 17. As a result, with regard to the aforementioned first conduit body 101A and second conduit body 103, the lengths of the conduit bodies can be modified to the state shown in FIG. 17 while the interior portion thereof remains watertight by actions of the aforementioned elastic member 104b.

With such an arrangement, an elastic member 104a is connected to the outer face of the aforementioned second conduit body 103 on the tip side thereof as shown in FIG. 18. The elastic member 104a can be moved integrally with the second conduit body 103. The elastic member 104a also maintains a watertight seal between the aforementioned second conduit body 103 and first conduit body 101A.

While description has been made in the present embodiment regarding an arrangement in which the aforementioned elastic member 104b is attached to the first conduit body 101A side, the present invention is not restricted to such an arrangement. Also, the elastic member may be attached to the second conduit body 103 side. Specifically, an arrangement may be made in which another elastic member 104a is provided so as to provide a watertight seal between the first conduit body 101A and the second conduit body 103.

On the other hand, the aforementioned second conduit body 103 includes a conduit portion 105 which forms a part of the aforementioned first conduit simulation portion 101A1 and a part of the aforementioned second conduit simulation portion 101A2 in the same way as with the aforementioned conduit portion 102 of the first conduit body 101A. With the present embodiment, the conduit portion 102 includes the two conduit portions 102a and 102b having different diameters. Accordingly, the aforementioned conduit portion 105 includes the two conduit portions 105a and 105b which communicate with the aforementioned conduit portions 102a and 102b, respectively. With such an arrangement, one of these conduit portions, the conduit portion 105a corresponds to the aforementioned first conduit simulation portion 101A1. The other conduit portion, i.e., the conduit portion 105b corresponds to the aforementioned second conduit simulation portion 101A2.

These two conduit portions 105a and 105b are inserted into the aforementioned two conduit portions 102a and 102b, respectively, as shown in FIG. 18. Furthermore, the base ends of these two conduit portions 105a and 105b are connected to the aforementioned second conduit body 103. Furthermore, elastic members 107 and 108 are connected to the tips thereof. These elastic members 107 and 108 maintain a watertight seal between the inner face of the conduit portion 102a and the outer face of the conduit portion 105a and between the inner face of the conduit portion 102b and the outer face of the conduit portion 105b, respectively.

With such an arrangement, the base end of the aforementioned conduit portion 105 is connected to the aforementioned second conduit body 103. Accordingly, upon the second conduit body 103 being moved from the position shown in FIG. 18 to the position shown in FIG. 19, the conduit portion 105 is moved from the position shown in FIG. 18 to the position shown in FIG. 19. This enables the lengths of the first and second conduit simulation portions 101A1 and 101A2 to be modified.

Such an arrangement including the aforementioned conduit portion 102 and conduit portion 105 allows the aforementioned lengths to be modified while the interior thereof remains watertight by actions of the elastic members 107 and 108. The elastic members 107 and 108 are connected to the conduit portion 105 as described above. Accordingly, the elastic members 107 and 108 are moved integrally with the conduit portion 105.

Note that, with regard to the sterilization confirmation tester 101 according to the present embodiment, the region 106 other than the conduit portion 102 of the first conduit body 101A may be configured in the form of a cavity, or may be filled with a certain material.

Furthermore, the aforementioned sterilization confirmation tester 101 is formed so as to be simulation of a medical device having conduits such as an endoscope or the like. Furthermore, CIs (or BIs) 109 and 109a are installed in the interior spaces of the aforementioned first conduit simulation portion 101A1 or the second conduit simulation portion 101A2 (the interior spaces of the conduit portions 102a and 105a, or the interior spaces of the conduit portions 102b and 105b). Alternatively, the CIs (or BIs) 109 and 109a are installed in the interior spaces of the aforementioned first conduit body 101A or the second conduit body 103 (the interior spaces of the conduit portions 102a and 102b, or the interior spaces of the conduit portions 105a and 105b).

Furthermore, all the members employed in the aforementioned sterilization confirmation tester 101 are formed of materials which enable these members to be subjected to treatment in the sterilization apparatus.

Next, description will be made regarding the operation of the sterilization confirmation tester according to the present embodiment with reference to FIG. 16 through FIG. 19.

It is assumed that confirmation of effective sterilization is made using the sterilization confirmation tester 101 according to the present embodiment after the sterilization treatment for a predetermined medical device such as an endoscope or the like. In this case, the CIs (or BIs) 109 and 109a are provided within the aforementioned conduit portion 102 and conduit portion 105 forming the aforementioned first and second conduit simulation portions 101A1 and 101A2 of the sterilization confirmation tester 101. In a case that a BI is employed as an indicator, the BI needs to be extracted in a sterile environment after the sterilization step. Accordingly, the conduit tester itself may be sealed with a seal pack or the like.

The operator adjusts the lengths of the first and second conduit simulation portions 101A1 and 101A2 as necessary so as to match the conduit length of the medical device to be tested, by sliding the first conduit body 101A or the second conduit body 103.

After the adjustment of the lengths of the first and second conduit simulation portions 101A1 and 101A2, the operator installs the aforementioned sterilization confirmation tester 101 which is a simulation of the conduit length of the medical device to be tested, in the sterilization apparatus, and sterilization step is executed according to a desired procedure.

For example, let us consider a case in which a steam pressure sterilization apparatus is employed as the aforementioned sterilization apparatus. In this case, steam infiltrates into the conduit portion 102 and the conduit portion 105 of the first conduit body 101A and the second conduit body 103. On the other hand, let us consider a case in which a gas sterilization apparatus is employed as the aforementioned sterilization apparatus. In this case, gas infiltrates into the conduit portion 102 and the conduit portion 105 of the first conduit body 101A and the second conduit body 103.

After the sterilization step, the operator extracts the aforementioned sterilization confirmation tester 101 from the sterilization apparatus, and extracts the CIs (or BIs) 109 and 109a from the conduit portion 102 or the conduit portion 105.

Then, in a case that the extracted indicator is a CI, the operator determines the effectiveness of sterilization of the aforementioned sterilization confirmation tester 101 according to a predetermined criterion (whether or not the color of the CI has changed, and so forth). In a case that the extracted indicator is a BI, the operator extracts the BI in a sterile environment, and the BI is introduced into a culture medium suitable for culturing. Then, effective sterilization is confirmed based upon whether or not a bacterial culture has appeared from the BI.

With such an arrangement, in the event that determination has been made that the aforementioned sterilization tester 101 has been sterilized, determination is made that the medical device to be tested can be sterilized by the aforementioned sterilization step. Conversely, in the event that determination has been made that the aforementioned conduit simulation portion has not been sterilized, determination is made that the medical device to be tested cannot be sterilized by the aforementioned sterilization step.

Note that, with the present embodiment, the medical device to be tested may be installed in the sterilization apparatus along with the aforementioned sterilization confirmation tester 101 at the same time.

Also, with the present embodiment, the aforementioned sterilization method is not restricted to high-pressure and high-temperature steam sterilization (autoclave sterilization) or EOG gas sterilization. Also, other sterilization methods may be employed. In this case, there is a need to employ an indicator such as the aforementioned CI or BI having a function of producing a reaction suitable for the sterilization method employed.

As can be understood from the above description, with the present embodiment, the sterilization confirmation tester 101 according to the present invention allows the lengths of the first and second conduit simulation portions 101A1 and 101A2 to be adjusted. Such an arrangement has a function of providing a simulation of the length of the conduit portion of medical devices having various kinds and lengths of the conduits such as an endoscope and so forth. This enables effective sterilization of the interior of the conduit of the medical device to be tested, such as an endoscope or the like, to be confirmed in a simple and sure manner after sterilization treatment by a desired sterilization apparatus.

Tenth Embodiment

Figure 20:
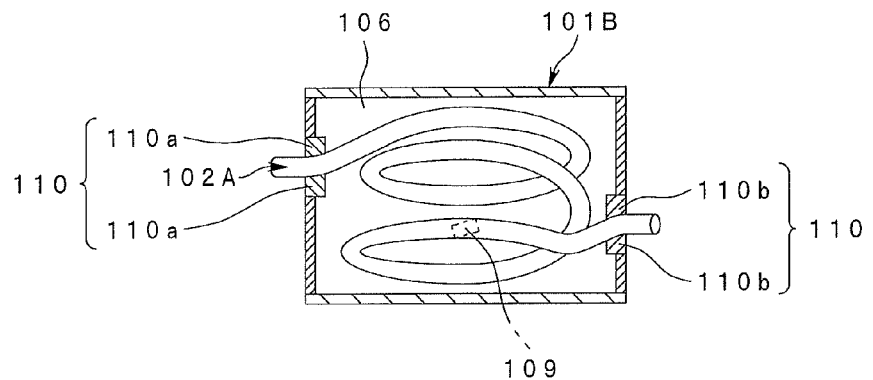
FIG. 20 shows a sterilization confirmation tester according a tenth embodiment of the present invention, and is a cross-sectional view which shows a schematic configuration of the sterilization confirmation tester including a conduit simulation portion having a predetermined length.
Figure 21:
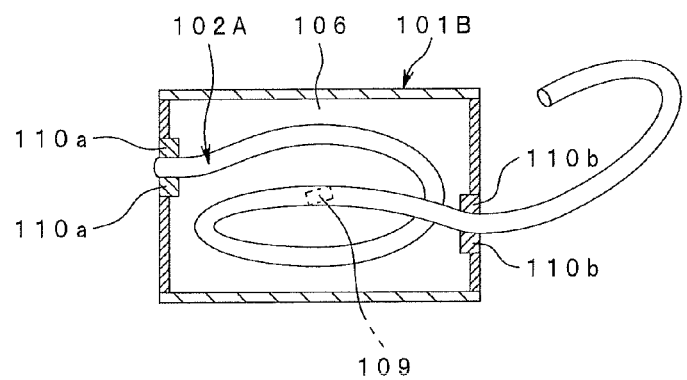
FIG. 21 is a cross-sectional view which shows a schematic configuration of the sterilization confirmation tester shown in FIG. 20, with the length of the conduit simulation portion having been adjusted by extracting the conduit simulation portion outward.

FIG. 20 and FIG. 21 show a sterilization confirmation tester according to a tenth embodiment of the present invention. FIG. 20 is a cross-sectional view which shows a schematic configuration of the sterilization confirmation tester including a conduit simulation portion having a predetermined length. FIG. 21 is a cross-sectional view which shows a schematic configuration of the sterilization confirmation tester with the length of the conduit simulation portion having been adjusted by extracting the conduit simulation portion outward. Note that, in FIG. 20 and FIG. 21, the same components as those of the aforementioned ninth embodiment are denoted by the same reference numerals, description thereof will be omitted, and description will be made regarding only the different components.

As shown in FIG. 20, a sterilization confirmation tester 101B according to the present embodiment includes a conduit simulation portion 102A which includes a conduit portion having a structure corresponding to the conduit of a medical device such as an endoscope or the like in the same way as with the aforementioned ninth embodiment. The difference is that the conduit simulation portion 102A is stored within the aforementioned sterilization confirmation tester 101B in a coil shape or an accordion-fold shape such that it remains not to bend sharply. Note that the length of the aforementioned conduit simulation portion 102A, which has been installed within the sterilization confirmation tester 101B beforehand, is inscribed on the outer face of the conduit simulation portion 102A. That is to say, the operator can confirm beforehand the initial length of the conduit simulation portion 102A stored within the sterilization confirmation tester 101B.

Furthermore, the aforementioned conduit simulation portion 102A is configured so as to allow it to be extracted from the base end side of the aforementioned sterilization confirmation tester 101B (right side in the drawing). That is to say, the aforementioned sterilization confirmation tester 101B is configured so as to allow the length of the conduit simulation portion 102A remaining in the sterilization confirmation tester 101B to be adjusted as necessary by extracting a portion of the conduit simulation portion 102A from the sterilization confirmation tester 101B, corresponding to the length of the conduit of an endoscope or the like to be tested, as shown in FIG. 21.

Note that, with regard to the conduit simulation portion 102A which remains within the sterilization confirmation tester 101B after the extraction step, one end thereof may be cut off at the insertion opening (insertion portion) of the aforementioned sterilization confirmation tester 101B on the tip end side thereof (left side in the drawing).

Elastic members or screws 110 are provided to the connection portions (insertion portion) where the conduit simulation portion 102A is connected to the sterilization confirmation tester 101B. The elastic members or screws 110 thus provided ensures that the interior of the sterilization confirmation tester 101B remains watertight. Note that elastic members or screws 110a are fit to the insertion opening of the aforementioned sterilization tester 101 on the tip end side. On the other hand, elastic members or screws 110b are fit to the extraction opening of the aforementioned sterilization tester 101 on the base end side.

With the sterilization confirmation tester 101B according to the present embodiment having such a configuration described above, the length of the conduit simulation portion 102A which remains within the sterilization confirmation tester 101B can be adjusted by extracting the conduit simulation portion 102A from the sterilization confirmation tester 101B as necessary corresponding to the length of the conduit of an endoscope or the like to be tested, in the same way as with the aforementioned ninth embodiment.

Note that, with regard to the sterilization confirmation tester 101B according to the present embodiment, the region 106 other than the conduit simulation portion 102A may be configured in the form of a cavity, or may be filled with a certain material.

Furthermore, the aforementioned sterilization confirmation tester 101B is formed so as to be a simulation of a medical device having conduits such as an endoscope or the like. Furthermore, CI (or BI) 109 is installed in the interior space within the aforementioned conduit simulation portion 102A.

Furthermore, all the members employed in the aforementioned sterilization confirmation tester 101B are formed of materials which enable these members to be subjected to treatment in the sterilization apparatus.

Next, description will be made regarding the operation of the sterilization confirmation tester according to the present embodiment with reference to FIG. 20 and FIG. 21.

It is assumed that confirmation is made with respect to effective sterilization of a predetermined medical device such as an endoscope and so forth using the sterilization confirmation tester according to the present embodiment. In this case, the CI (or BI) 109 is provided within the aforementioned conduit simulation portion 102A of the sterilization confirmation tester 101B. In a case that a BI is employed as an indicator, the BI needs to be extracted in a sterile environment after the sterilization step. Accordingly, the conduit tester itself may be sealed within a seal pack or the like.

The operator adjusts the length of the conduit simulation portion 102A which remains within the sterilization confirmation tester 101B as necessary so as to match the conduit length of the medical device to be tested, by extracting the tip of the conduit simulation portion 102A from the extraction opening formed on the base end side of the sterilization confirmation tester 101B.

After the adjustment of the length of the conduit simulation portion, the operator installs the aforementioned sterilization confirmation tester 101B, which is a simulation of the conduit length of the medical device to be tested, in the sterilization apparatus, and the sterilization step is executed according to a desired procedure.

For example, let us consider a case in which a steam pressure sterilization apparatus is employed as the aforementioned sterilization apparatus. In this case, steam infiltrates into the conduit simulation portion 102A of the sterilization confirmation tester 101B. On the other hand, let us consider a case in which a gas sterilization apparatus is employed as the aforementioned sterilization apparatus. In this case, gas infiltrates into the conduit simulation portion 102A of the sterilization confirmation tester 101B. Then, the steam or gas acts upon the CI (or BI) 109 installed in the conduit simulation portion 102A.

After the sterilization step, the operator extracts the aforementioned sterilization confirmation tester 101B from the sterilization apparatus, and extracts the CI (or BI) 109 from the conduit simulation portion 102A.

Then, in a case that the extracted indicator is a CI, the operator determines the effectiveness of sterilization of the aforementioned sterilization confirmation tester 101B according to a predetermined sterilization criterion (whether or not the color of the CI has changed, and so forth). In a case that the extracted indicator is a BI, the operator extracts the BI in a sterile environment, and the BI is introduced into a culture medium suitable for culturing the BI. Then, effective sterilization is confirmed based upon whether or not a bacterial culture has appeared from the BI.

With such an arrangement, in the event that determination has been made that the aforementioned sterilization tester 101B has been sterilized, determination is made that the medical device to be tested can be sterilized by the aforementioned sterilization step. Conversely, in the event that determination has been made that the aforementioned conduit body has not been sterilized, determination is made that the medical device to be tested cannot be sterilized by the aforementioned sterilization step.

Note that, with the present embodiment, the medical device to be tested may be installed in the sterilization apparatus along with the aforementioned sterilization confirmation tester 101B at the same time.

Also, with the present embodiment, the aforementioned sterilization method is not restricted to high-pressure and high-temperature steam sterilization (autoclave sterilization) or EOG gas sterilization. Also, other sterilization methods may be employed. In this case, there is a need to employ an indicator such as the aforementioned CI or BI having a function of producing a reaction suitable for the sterilization method employed.

Thus, the present embodiment having such a configuration described above is fully capable of corresponding to a medical device which has a long conduit. This provides the advantage of expanding the range of usage thereof, as well as the same advantages as those of the aforementioned ninth embodiment.

Eleventh Embodiment

Figure 22:
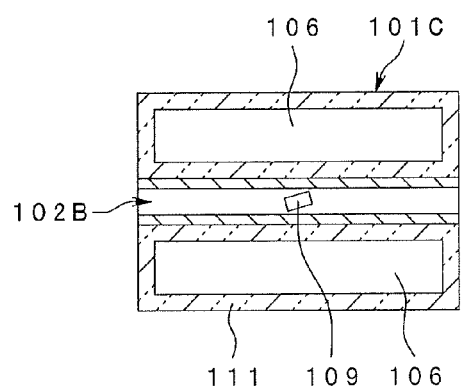
FIG. 22 is a cross-sectional view which shows a schematic configuration of a sterilization confirmation tester according to an eleventh embodiment of the present invention.

FIG. 22 shows a sterilization confirmation tester according to an eleventh embodiment of the present invention, and is a cross-sectional view which shows a schematic configuration of the sterilization confirmation tester. Note that, in FIG. 22, the same components as those of the aforementioned ninth embodiment are denoted by the same reference numerals, description thereof will be omitted, and description will be made regarding only the different components.

As shown in FIG. 22, a sterilization confirmation tester 101C according to the present embodiment has generally the same configuration as that of the sterilization confirmation tester 101 according to the aforementioned ninth embodiment, or that of the sterilization confirmation tester 101B according to the aforementioned tenth embodiment, except for the following difference. That is to say, the difference is that at least one of the sterilization confirmation tester 101C and a conduit simulation portion 102B includes a thermal insulating member 111 for suppressing the flow of heat to/from the aforementioned conduit simulation portion 102B. Accordingly, the thermal insulating member 111 is provided so as to cover the entire region of or a part of the outer face of the conduit simulation portion 102B.

Note that the aforementioned thermal insulating member 111 may be formed of a member forming a flexible hose of an endoscope.

Also, the sterilization confirmation tester 101C according to the present embodiment is a simulation of a medical device having conduits such as an endoscope and so forth, and a CI (or BI) 109 is installed in the interior of the aforementioned conduit simulation portion 102B, in the same way as with the aforementioned two embodiments, i.e., the ninth and tenth embodiments.

The other components are the same as those of the ninth embodiment and the tenth embodiment.

Also, the sterilization confirmation tester according to the present embodiment operates in generally the same way as with the ninth embodiment and the tenth embodiment described above.

As described above, the sterilization confirmation tester according to the present embodiment has a function of enabling the length of the conduit simulation portion 102B to be adjusted in the same way as with the ninth embodiment and the tenth embodiment described above. In addition, the sterilization confirmation tester according to the present embodiment includes the thermal insulating member 111 for reducing the thermal conductivity, thereby suppressing the flow of heat to/from the conduit simulation portion 102B. Such an arrangement can simulate the thermal conductivity of the conduit portion of medical devices such endoscopes and the length of the conduit portion of medical devices, such as endoscopes, having various kinds and lengths of conduits. This enables effective sterilization for the interior of the conduit of the medical device to be tested, such as an endoscope or the like, to be confirmed in a simple and sure manner after sterilization treatment by a desired sterilization apparatus.

Twelfth Embodiment

Figure 23:
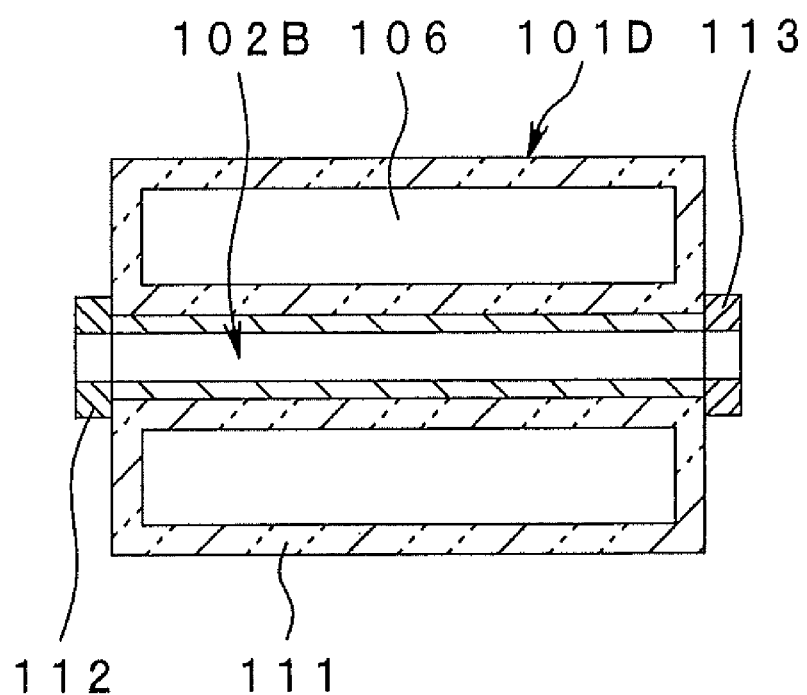
FIG. 23 is a cross-sectional view which shows a schematic configuration of a sterilization confirmation tester according to a twelfth embodiment of the present invention.
Figure 24:
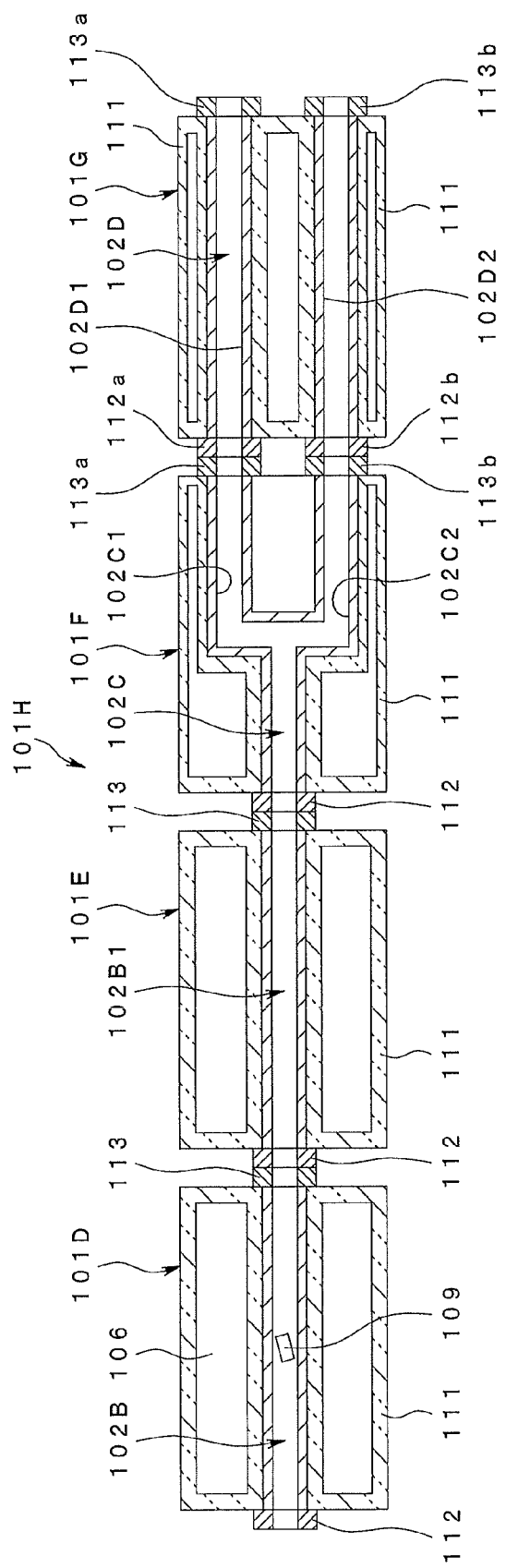
FIG. 24 is a cross-sectional view which shows a configuration of a sterilization confirmation tester formed of multiple sterilization confirmation test units shown in FIG. 23, which are connected so as to communicate with one another.

FIG. 23 and FIG. 24 show a sterilization confirmation tester according to a twelfth embodiment of the present invention. FIG. 23 is a cross-sectional view which shows a schematic configuration of the sterilization confirmation test unit. FIG. 24 is a cross-sectional view which shows a configuration of a sterilization confirmation tester formed of multiple sterilization confirmation test units shown in FIG. 23, which are connected so as to communicate with one another. Note that, in FIG. 23 and FIG. 24, the same components as those of the aforementioned eleventh embodiment are denoted by the same reference numerals, description thereof will be omitted, and description will be made regarding only the different components.

As shown in FIG. 23, a sterilization confirmation test unit 101D according to the present embodiment has generally the same configuration as that of the sterilization confirmation tester 101C. With the present embodiment, multiple sterilization test units having different conduit simulation portions including the aforementioned sterilization confirmation test unit 101D are connected so as to communicate with one another. Such an arrangement provides an improved sterilization confirmation tester having a function of allowing the overall length of the conduit simulation portion to be adjusted in the longitudinal direction.

That is to say, the sterilization confirmation test unit 101D according to the present embodiment includes connection portions 112 and 113 for connecting so as to communicate the conduit simulation portion 102B with a different conduit simulation portion (conduit portion). These connection portions 112 and 113 are fit to the opening portions on both sides of the aforementioned conduit simulation portion 102B in a watertight manner. Note that these connection portions 112 and 113 are configured in the form of a screw structure, for example. In this case, an arrangement may be made in which one of these connection portions is configured in the form of a male screw, and the other connection portion is configured in the form of a female screw.

With the present embodiment, let us consider a case in which the aforementioned sterilization confirmation test unit 101D is connected to another sterilization confirmation test unit 101E as shown in FIG. 24, for example. In this case, upon connecting the connection portion 113 of the sterilization confirmation test unit 101D to the connection portion 112 of the sterilization confirmation test unit 101E, the conduit simulation portion 102B communicates with a conduit simulation portion 102B1 while maintaining a watertight connection between the sterilization confirmation test unit 101D and the sterilization confirmation test unit 101E.

In a case of using a sterilization confirmation test unit 101F shown in FIG. 24, having a structure in which a conduit simulation portion 102C bifurcates, an arrangement may be made in which one side face (opening portion) has a single connection portion 112, and the other side face (opening portion) has two connection portions, e.g., a connection portion 113a and a connection portion 113b.

With such an arrangement, the sterilization confirmation test unit 101F can be connected to a sterilization confirmation test unit 101G. The sterilization confirmation test unit 101G includes two conduit simulation portions 102D1 and 102D2 which are to be connected so as to communicate with two conduit simulation portions 102C1 and 102C2, respectively, which are included in the sterilization confirmation test unit 101F. The sterilization confirmation test unit 101G is configured so as to have the connection portions 112a, 112b, 113a, and 113b, formed on both side faces corresponding to the opening portions of these conduit simulation portions 102D1 and 102D2. As described above, with the present embodiment, the sterilization confirmation test unit may have a predetermined number of the connection portions, with the number of the connection portions matching the number of the opening portions of the conduit simulation portions.

The other components are the same as those of the aforementioned eleventh embodiment.

Next, description will be made regarding the operation of the sterilization confirmation tester according to the present embodiment with reference to FIG. 23 and FIG. 24.

It is assumed that confirmation is made with respect to effective sterilization of a predetermined medical device such as an endoscope and so forth using the sterilization confirmation tester according to the present embodiment. In this case, one or each of the aforementioned conduit simulation portions 102B, 102B1, 102C, 102C1, 102C2, 102D1, and 102D2 stores a CI (or BI) 109 therewithin. In a case that a BI is employed as an indicator, the BI needs to be extracted in a sterile environment after the sterilization step. Accordingly, the conduit testers 101D and 101H themselves may be sealed with a seal pack or the like.

The operator selects the sterilization confirmation test units from among the various different types (e.g., a type such as the sterilization confirmation test unit 101D having a single conduit simulation portion, a type such as the sterilization confirmation test unit 101F having a structure in which a conduit simulation portion is divided into two (102C1, 102C2) or more, and a type such as the sterilization confirmation test unit 101G having two conduit simulation portions (102D1, 102D2), corresponding to the conduit structure of the medical device to be tested. Furthermore, the operator determines the order of connection therebetween such that the sterilization confirmation tester is a simulation of the conduit structure of the medical device to be tested.

For example, in a case where the operator disposes the sterilization confirmation test units as shown in FIG. 24, the operator connects the sterilization confirmation test unit 101D and the sterilization confirmation test unit 101E with each other through the connection portion 113 and the connection portion 112 such that the conduit simulation portion 102B and the conduit simulation portion 102B1 communicate with each other. Subsequently, the operator connects the sterilization confirmation test unit 101E and the sterilization confirmation test unit 101F with each other through the connection portion 113 and the connection portion 112 in the same way. Furthermore, the operator connects the sterilization confirmation test unit 101F and the sterilization confirmation test unit 101G with each other through the connection portions 113*a* and 113*b* and the connection portions 112*a* and 112*b* in the same way, thereby forming the sterilization confirmation tester 101H according to the present embodiment. With such an arrangement, these sterilization confirmation units are connected so as to communicate with one another while maintaining the interior thereof in a watertight state.

Subsequently, after assembly of the sterilization confirmation tester 101H so as to be a simulation of the conduit structure of the medical device to be tested, the operator installs the sterilization confirmation tester 101H in the sterilization apparatus, and the desired sterilization treatment is executed.

For example, let us consider a case in which a steam pressure sterilization apparatus is employed as the aforementioned sterilization apparatus. In this case, steam infiltrates into the conduit simulation portions 102B, 102B1, 102C, 102C1, 102C2, 102D1, and 102D2 of the sterilization confirmation tester 101H. On the other hand, let us consider a case in which a gas sterilization apparatus is employed as the aforementioned sterilization apparatus. In this case, gas infiltrates into the conduit simulation portions 102B, 102B1, 102C, 102C1, 102C2, 102D1, and 102D2 of the sterilization confirmation tester 101H. Then, the steam or gas acts upon the CIs (or BIs) 109 installed in the conduit simulation portions.

After the sterilization step, the operator extracts the aforementioned sterilization confirmation tester 101H from the sterilization apparatus, and extracts the CI (or BI) 109 from the aforementioned conduit simulation portion.

Then, in a case that the extracted indicator is a CI, the operator determines the effectiveness of sterilization of the aforementioned sterilization confirmation tester 101H according to a predetermined criterion (whether or not the color of the CI has changed, and so forth). In a case that the extracted indicator is a BI, the operator extracts the BI in a sterile environment, and the BI is introduced into a culture medium suitable for culturing the BI. Then, effective sterilization is confirmed based upon whether or not a bacterial culture has appeared from the BI.

With such an arrangement, in the event that determination has been made that the aforementioned sterilization tester 101H has been sterilized, determination is made that the medical device to be tested can be sterilized by the aforementioned sterilization step. Conversely, in the event that determination has been made that the sterilization tester 101H has not been sterilized, determination is made that the medical device to be tested cannot be sterilized by the aforementioned sterilization step.

Note that, with the present embodiment, the medical device to be tested may be installed in the sterilization apparatus along with the aforementioned sterilization confirmation tester 101H at the same time.

Also, with the present embodiment, the aforementioned sterilization method is not restricted to high-pressure and high-temperature steam sterilization (autoclave sterilization) or EOG gas sterilization. Also, other sterilization methods may be employed. In this case, there is a need to employ an indicator such as the aforementioned CI or BI having a function of producing a reaction suitable for the sterilization method employed.

As can be understood from the above description, with the present embodiment, the sterilization confirmation tester 101H has a function of simulating the conduit portion of medical devices such as endoscopes and so forth. This enables effective sterilization of the interior of the conduit of the medical device to be tested, such as an endoscope or the like, to be confirmed in a simple and sure manner after sterilization treatment by a desired sterilization apparatus.

Thirteenth Embodiment

Figure 25:
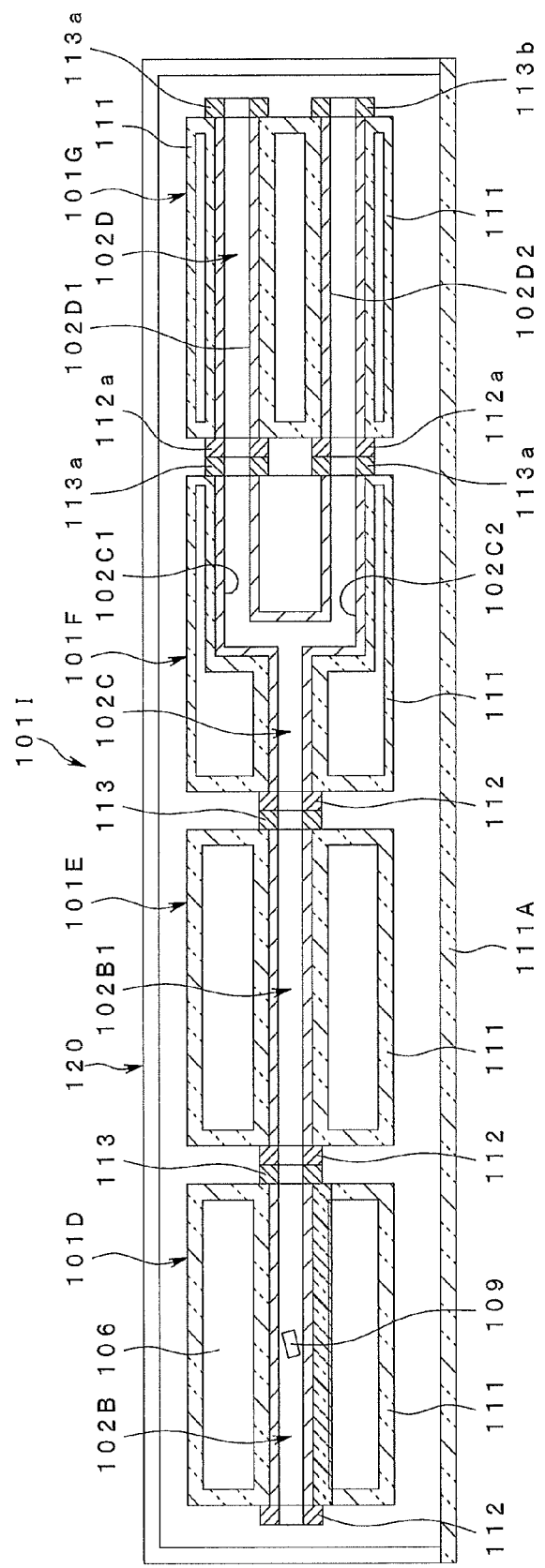
FIG. 25 is a cross-sectional view which shows a schematic configuration of a sterilization confirmation test pack employing a sterilization confirmation tester according to a thirteenth embodiment of the present invention.
Figure 26:
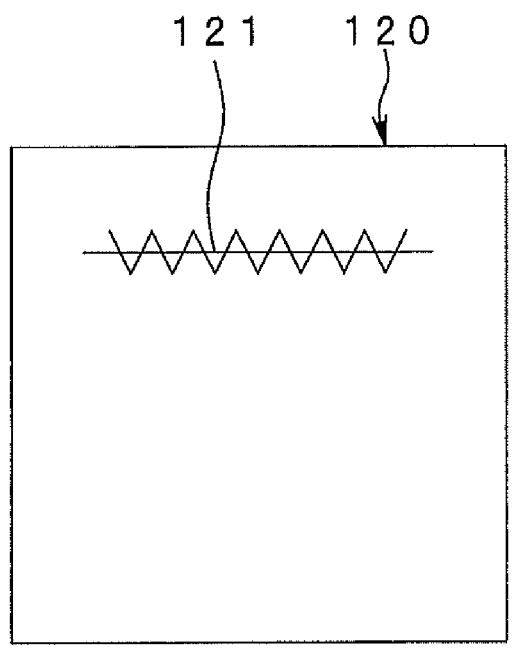
FIG. 26 is an external view which shows a sterilization confirmation test pack including opening/closing means.

FIG. 25 and FIG. 26 show a sterilization confirmation tester according to a thirteen embodiment of the present invention. FIG. 25 is a cross-sectional view which shows a schematic configuration of a sterilization confirmation test pack employing a sterilization confirmation tester. FIG. 26 is an external view which shows a sterilization confirmation test pack including opening/closing means. Note that, in FIG. 25, the same components as those of the aforementioned twelfth embodiment are denoted by the same reference numerals, description thereof will be omitted, and description will be made regarding only the different components.

As shown in FIG. 25 and FIG. 26, a sterilization confirmation test pack 101I includes: the sterilization confirmation tester 101H having the same configuration as that of the aforementioned thirteenth embodiment; and a packaging member 120 for storing the sterilization confirmation tester 101H.

Note that, with the present embodiment, the aforementioned sterilization confirmation tester 101H stored in the packaging member 120 has a structure in which multiple sterilization confirmation test units are connected so as to communicate with one another. However, the present invention is not restricted to a particular arrangement such as this. Also, the operator can select a desired number of the sterilization confirmation test units having desired structures from among the aforementioned sterilization confirmation test units (see FIG. 24) and can connect these sterilization confirmation test units thus selected so as to communicate with one another such that the sterilization confirmation tester 101H is a simulation of the conduit structure of the medical device to be tested.

The aforementioned packaging member 120 is configured so as to store part of or all of the aforementioned sterilization test units 101D through 101G. Such an arrangement may or may not allow the aforementioned sterilization confirmation tester 101H to be inserted/extracted.

Also, the aforementioned packaging member 120 may be configured so as to include a thermal insulating member 111A for reducing the thermal conductivity thereof as shown in FIG. 25, thereby suppressing the flow of heat to/from the sterilization confirmation tester 101H or the conduit simulation portions 102B (102B1, 102C, 102C1, 102C2, 102D1, 102D2).

Note that, with the present embodiment, the aforementioned packaging member 120 may be configured so as to include a filter, which has the nature of allowing steam, gas, and so forth, to pass therethrough, or a film, which has the nature of preventing steam, gas, and so forth, from passing therethrough, provided to at least a part of thereof. Also, an arrangement may be made in which the whole of the packaging member 120 is formed of a transparent member. This allows visual confirmation of the sterilization confirmation tester 101H stored therein to be made immediately.

Also, the aforementioned thermal insulating member 111A may be formed of the same member as that forming a flexible hose of an endoscope which is a medical device.

Also, the sterilization confirmation test pack 101I according to the present embodiment may include the opening/closing means 121 provided to the aforementioned packaging member 120 as shown in FIG. 26, thereby allowing the sterilization confirmation tester 101H, which is to be stored therewithin, to be inserted/extracted. With such an arrangement, the aforementioned opening/closing means 121 need to be configured so as to ensure that the interior of the aforementioned packaging member 120 remains watertight.

The other components are the same as those of the aforementioned thirteenth embodiment.

Next, description will be made regarding the operation of the sterilization confirmation test pack according to the present embodiment with reference to FIG. 25 and FIG. 26. Note that the operation of the sterilization confirmation test pack according to the present embodiment is generally the same as that according to the aforementioned thirteenth embodiment. Accordingly, description will be made regarding only the different components from the aforementioned thirteenth embodiment.

After assembly of the sterilization confirmation tester 101H having a structure in which the multiple sterilization confirmation testers 101D through 101G are connected so as to communicate with one another, and so as to be a simulation of the conduit structure of the medical device to be tested, the operator wraps so as to cover a part of or all of the aforementioned sterilization confirmation tester 101H in the packaging member 120.

In this case, an arrangement may be made in which a part of or all of the sterilization confirmation tester 101H is wrapped so as to be covered by the packaging member 120 beforehand. Also, the packaging member 120 may include the aforementioned opening/closing means 121, thereby allowing the operator to store the aforementioned sterilization confirmation tester 101H in the packaging member 120 through the opening/closing means 121.

After the sterilization step, the operator extracts the aforementioned sterilization confirmation test pack 101I including the sterilization confirmation tester 101H from the sterilization apparatus. Then, the operator extracts the sterilization confirmation tester 101H from the packaging member 120. In this stage, in a case that the aforementioned packaging member 120 includes the opening/closing means 121, the operator can extract the sterilization confirmation tester 101H stored therewithin through the opened opening/closing means 121.

Subsequently, the operator extracts the CI (or BI) 109 from the aforementioned conduit simulation portion 102B of the sterilization confirmation tester 101H thus extracted.

Then, in a case that the extracted indicator is a CI, the operator determines the effectiveness of sterilization of the aforementioned sterilization confirmation tester 101H according to a predetermined criterion (whether or not the color of the CI has changed, and so forth). In a case that the extracted indicator is a BI, the operator extracts the BI in a sterile environment, and the BI is introduced into a culture medium suitable for culturing the BI. Then, effective sterilization is confirmed based upon whether or not a bacterial culture has appeared from the BI.

With such an arrangement, in the event that determination has been made that the aforementioned sterilization tester 101H has been sterilized, determination is made that the medical device to be tested can be sterilized by the aforementioned sterilization step. Conversely, in the event that determination has been made that the sterilization tester 101H has not been sterilized, determination is made that the medical device to be tested cannot be sterilized by the aforementioned sterilization step.

Note that, with the present embodiment, the medical device to be tested may be installed in the sterilization apparatus along with the aforementioned sterilization confirmation test pack 101I at the same time.

Also, with the present embodiment, the aforementioned sterilization method is not restricted to high-pressure and high-temperature steam sterilization (autoclave sterilization) or EOG gas sterilization. Also, other sterilization methods may be employed. In this case, there is a need to employ an indicator such as the aforementioned CI or BI having a function of producing a reaction suitable for the sterilization method employed.

Thus, with the present embodiment having such a configuration described above, the sterilization confirmation test pack 101I has a function of simulating the conduit portion of medical devices such as endoscopes and so forth, while providing a function as a simply handled test pack. This enables effective sterilization of the interior of the conduit of the medical device to be tested, such as an endoscope or the like, to be confirmed in a simple and sure manner after sterilization treatment by a desired sterilization apparatus.

The sterilization confirmation tester and the sterilization confirmation test pack employing such a sterilization confirmation tester according to the ninth embodiment through the thirteenth embodiment described above provides the advantage of allowing confirmation of effective sterilization to be made in a simple and sure manner with respect to the interior of the conduit of medical devices having various kinds of conduit structures such as endoscopes and so forth.

The sterilization confirmation tester and the sterilization confirmation test pack employing such a sterilization confirmation tester according to the present invention provide the advantage of allowing confirmation of effective sterilization to be made in a simple and sure manner with respect to the interior of the conduit of medical devices having various kinds of conduit structures such as endoscopes and so forth. Such an arrangement is particularly effective in a case in which endoscopic examination followed by reprocessing of the endoscope is repeatedly performed in the course of a day using a single endoscope.

Note that the present invention is not restricted to the first through thirteenth embodiments described above. Rather, various modification may be made without departing from the spirit and scope of the invention.

What is claimed is:

1. A sterilization confirmation tester for confirming effective sterilization performed by a sterilization apparatus for generating a sterilization agent, the sterilization confirmation tester comprising:
    an indicator casing for storing an indicator for confirming an effect of sterilization;
    two conduit tubes, each having one end connected to the indicator casing so as to communicate with the interior thereof and having a conduit shape corresponding to a conduit of an endoscope: and
    an outer cover member for holding both of the other ends of the two conduit tubes connected to the indicator casing such that the sterilization agent can enter from both of the other ends of the two conduit tubes in communication with the exterior and reach the interior of the indicator casing, the outer casing member enclosing the indicator casing in an interior of the outer cover member in a watertight manner, and being formed of a material exhibiting the same thermal insulating effect as that of a flexible hose or an operating unit of the endoscope, wherein both of the other ends of the two conduit tubes are held by the outer cover member such that the indicator casing and outer surfaces of the two conduit tubes are not in contact with an inner surface of the outer cover member in the interior of the outer cover member.

2. The sterilization confirmation tester according to claim 1, wherein the outer cover member has a tubular structure.

3. The sterilization confirmation tester according to claim 2, wherein the other ends of the two conduit tubes are respectively held in watertight states at ends of the tubular structure.

4. The sterilization confirmation tester according to claim 1, wherein the outer cover member includes two members, one of the two members having two through holes, and the other ends of the two conduit tubes are detachably insertable into the two through holes, respectively, the other ends being inserted into the two through holes in watertight states.

5. The sterilization confirmation tester according to claim 1, wherein the outer cover member has an approximately spherical shape or box shape that is formed by a combination of two members.

* * * * *